(12) United States Patent
Mostov et al.

(10) Patent No.: US 11,439,695 B2
(45) Date of Patent: Sep. 13, 2022

(54) KIDNEY INJURY TREATMENT

(71) Applicants: The Regents of the University of California, Oakland, CA (US); Fudan University, Shanghai (CN)

(72) Inventors: Keith E. Mostov, San Francisco, CA (US); Liang Cai, Shanghai (CN)

(73) Assignees: The Regents of the University of California, Oakland, CA (US); Fudan University, Shanghai (CN)

( * ) Notice: Subject to any disclaimer, the term of this patent is extended or adjusted under 35 U.S.C. 154(b) by 0 days.

(21) Appl. No.: 17/151,027

(22) Filed: Jan. 15, 2021

(65) Prior Publication Data

US 2021/0138047 A1    May 13, 2021

Related U.S. Application Data

(63) Continuation of application No. PCT/US2019/041664, filed on Jul. 12, 2019.

(60) Provisional application No. 62/699,944, filed on Jul. 18, 2018.

(51) Int. Cl.
| | | |
|---|---|---|
| *A61K 38/57* | (2006.01) | |
| *A61K 47/60* | (2017.01) | |
| *A61P 13/12* | (2006.01) | |

(52) U.S. Cl.
CPC .............. *A61K 38/57* (2013.01); *A61K 47/60* (2017.08); *A61P 13/12* (2018.01)

(58) Field of Classification Search
CPC ................................ A61P 13/12; A61K 38/57
See application file for complete search history.

(56) References Cited

U.S. PATENT DOCUMENTS

| | | |
|---|---|---|
| 2014/0038203 A1 | 2/2014 | Arthur et al. |
| 2014/0315734 A1 | 10/2014 | Arnold et al. |
| 2016/0033512 A1 | 2/2016 | Hellstrom et al. |
| 2018/0177840 A1 | 6/2018 | Szeto et al. |

OTHER PUBLICATIONS

International Application No. PCT/US2019/041664, International Search Report and Written Opinion dated Oct. 2, 2019, 7 pages.

*Primary Examiner* — Lianko G Garyu
(74) *Attorney, Agent, or Firm* — Kilpatrick Townsend & Stockton LLP

(57) ABSTRACT

Methods and compositions for treating kidney injury are provided.

8 Claims, 7 Drawing Sheets

Specification includes a Sequence Listing.

KIDNEY INJURY TREATMENT

CROSS-REFERENCED TO RELATED PATENT APPLICATIONS

The present application is a continuation of International Application No. PCT/US2019/041664, filed Jul. 12, 2019, which claims benefit of priority to U.S. Provisional Patent Application No. 62/699,944, filed on Jul. 18, 2018, each of which are incorporated by reference for all purposes.

STATEMENT AS TO RIGHTS TO INVENTIONS MADE UNDER FEDERALLY SPONSORED RESEARCH AND DEVELOPMENT

This invention was made with government support under grant no. R01 DK074398 awarded by the National Institutes of Health. The government has certain rights in the invention.

REFERENCE TO A "SEQUENCE LISTING," A TABLE, OR A COMPUTER PROGRAM LISTING APPENDIX SUBMITTED ON A COMPACT DISK

This application is being filed electronically and includes an electronically submitted sequence listing in .txt format. The .txt file contains a sequence listing entitled "081906-1230734-226710US_SL" created on Feb. 23, 2022 and having a size of 16,912 bytes. The sequence listing contained in this .txt file is part of the specification and is herein incorporated by reference in its entirety.

BACKGROUND OF THE INVENTION

Acute kidney injury (AKI) is an enormous unmet clinical problem. It occurs in 1-7% of hospitalizations and up to 58% of Intensive Care Unit (ICU) admissions. Mortality can be as high as 50-70% of ICU patients. A 4-year survey in a tertiary metropolitan hospital reported a 3% overall incidence rate of AKI, and a nearly 10-fold increase of in-hospital mortality for patients with AKI. AKI is a major contributor to the progression of chronic kidney disease. AKI is more common in the elderly and, as the elderly population is increasing, AKI is becoming more common.

The causes of AKI are complex and it usually occurs secondarily to other conditions, such as sepsis, cardiovascular disease, major surgery, etc. On the cellular level, hypoxia or toxins in renal tubules induces apoptosis and/or necrosis of renal tubular epithelial cells; severe damage of these cells is the hallmark of AKI (Devarajan, P., *J Am Soc Nephrol* 17, 1503-1520 (2006); Thadhani, R., et al. *N Engl J Med* 334, 1448-1460 (1996)).

Despite decades of study, there is no specific therapy for AKI. The only therapy is supportive care. Recovery after AKI is driven by dedifferentiation, proliferation and redifferentiation of the remaining tubular epithelial cells or progenitor cells, but not by stem cells from outside of the kidney. Notch signaling (Gupta, S. et al. *Am J Physiol Renal Physiol* 298, F209-215 (2010)) and Wnt signaling (Lin, S. L. et al. *Proc Natl Acad Sci USA* 107, 4194-4199 (2010)) have been reported to play roles in renal recovery. Yet, no intervention has been reported to promote recovery from AKI.

BRIEF SUMMARY OF THE INVENTION

In some embodiments, a method of treating acute kidney injury (or injury to a different epithelial or non-epithelial tissue) in a human. In some embodiments, the method comprising administering to the human a sufficient amount of a polypeptide comprising an amino acid sequence at least 70% (e.g., 75%, 80%, 85%, 90%, 95%, 97%, 99%, or 100%) identical to SEQ ID NO:1 or any protein in Table A or Table B, or an active fragment thereof, to reduce at least one symptom of the acute kidney injury. In some embodiments, the polypeptide comprises SEQ ID NO:1 or an active fragment thereof. In some embodiments, the amino acid sequence is linked to a protein sequence that extends the circulating half-life of the polypeptide. In some embodiments, the amino acid sequence is linked to an antibody Fc domain or human serum albumin. In some embodiments the amino acid sequence is linked to an antibody Fc domain that has been mutated to prolong the circulating half-life of polypeptide. In some embodiments, the polypeptide is PEGylated. In some embodiments, the polypeptide comprises at least one non-naturally-encoded amino acid. In some embodiments, the polypeptide is administered intravenously, by injection, intramuscularly, parenterally, intraperitoneally, orally, inhalationally, nasally, rectally, transdermally or by any other method used to administer a pharmacological agent.

Definitions

A "WFDC2 protein" or WFDC2 polypeptide" as used herein refers to a protein comprising a WFDC domain, also known as a WAP Signature motif, that contains eight cysteines forming four disulfide bonds at the core of the protein. The WFDC2 protein is sometimes referred to as the "Human Epididymis Protein-4," that is sometimes abbreviated as "HE4." In some embodiments, the WFDC domain functions as a protease (peptidase) inhibitor. Exemplary WFDC2 polypeptides include any isoform from humans, including but not limited to isoform 1

```
(MPACRLGPLAAALLLSLLLFGFTLVSGTGAEKTGVCPELQADQNCT

QECVSDSECADNLKCCSAGCATFCSLPNDKEGSCPQVNINFPQLGLC

RDQCQVDSQCPGQMKCCRNGCGKVSCVTPNF; SEQ ID NO: 1)
``` and active variants, truncations and fusions there.

Exemplary WFDC2 proteins from other species include, e.g.,

```
> WFDC2_CANLF (Canis lupus familiaris)
                                        (SEQ ID NO: 2)
MPACRPGPLAGALLLGLLLLGLPRVPGGEVEKTGVCPQLQADLNCTQ

ECVSDAQCADNLKCCQAGCATICHLPNEKEGSCPQVNTDFPQLGLCQ

DQCQVDSHCPGLLKCCYNGCGKVSCVTPIF

> WFDC2_RABIT (Oryctolagus cuniculus)
                                        (SEQ ID NO: 3)
MPASRLVPLGAVLLLGLLLLLELPPVTGTGADKPGVCPQLSADLNCT

QDCRADQDCAENLKCCRAGCSAICSIPNEKEGSCPSIDFPQLGICQD

LCQVDSQCPGKMKCCLNGCGKVSCVTPNF

> WFDC2_RAT (Rattus norvegicus)
                                        (SEQ ID NO: 4)
MPACRLCLLATGLLLGLLLFTPLSATGTRAEKPGVCPQLEPITDCVK

ACILDNDCQDNYKCCQAGCGSVCSKPNGLSEGKLSRTATGTTTLSAG
```

-continued

LARTSPLSRGQVSTKPPVVTKEGGNGEKQGTCPSVDFPKLGLCEDQC

QMDSQCSGNMKCCRNGCGKMGCTTPKF

> WFDC2_MOUSE (Mus musculus)
(SEQ ID NO: 5)
MPACRLCLLAAGLLLGLLLFTPISATGTDAEKPGECPQLEPITDCVL

ECTLDKDCADNRKCCQAGCSSVCSKPNGPSEGELSGTDTKLSETGTT

TQSAGLDHTTKPPGGQVSTKPPAVTREGLGVREKQGTCPSVDIPKLG

LCEDQCQVDSQCSGNMKCCRNGCGKMACTTPKF

> WFDC2_PIG (Sus scrofa)
(SEQ ID NO: 6)
MPACRLGLLVASLLLGLLLGLPPVTGTGAEKSGVCPAVEVDMNCTQE

CLSDADCADNLKCCKAGCVTICQMPNEKEGSCPQVDIAFPQLGLCLD

QCQVDSQCPGQLKCCRNGCGKVSCVTPVF

These sequences can be aligned as follows (SEQ ID NOS 1-6, respectively, in order of appearance):

```
Q14508|WFDC2_HUMAN  MPACRLGPLAAALLLSLL-LFGFTLVSGTGAEKTGVCPELQADQNCTQECVSDSECADNL   59
Q28894|WFDC2_CANLF  MPACRPGPLAGALLLGLL-LLGLPRVPGGEVEKTGVCPQLQADLNCTQECVSDAQCADNL   59
Q28631|WFDC2_RABIT  MPASRLVPLGAVLLLGLLLLLELPPVTGTGADKPGVCPQLSADLNCTQDCRADQDCAENL   60
Q8CHN3|WFDC2_RAT    MPACRLCLLATGLLLGLLL-FTPLSATGTRAEKPGVCPQLEPITDCVKACILDNDCQDNY   59
Q9DAU7|WFDC2_MOUSE  MPACRLCLLAAGLLLGLLL-FTPISATGTDAEKPGECPQLEPITDCVLECTLDKDCADNR   59
Q8MI69|WFDC2_PIG    MPACRLGLLVASLLLGL--LLGLPPVTGTGAEKSGVCPAVEVDMNCTQECLSDADCADNL   58
                    ***.*    *   ***.*     .   *    .:* * **   :.    :*.   *   * :*  :*

Q14508|WFDC2_HUMAN  KCCSAGCATFCSLPN---------------------------------------------   74
Q28894|WFDC2_CANLF  KCCQAGCATICHLPN---------------------------------------------   74
Q28631|WFDC2_RABIT  KCCRAGCSAICSIPN---------------------------------------------   75
Q8CHN3|WFDC2_RAT    KCCQAGCGSVCSKPNGLSEGKLSRT-----ATGTTTLSAGLARTSPLSRGQVSTKPPVVT  114
Q9DAU7|WFDC2_MOUSE  KCCQAGCSSVCSKPNGPSEGELSGTDTKLSETGTTTQSAGLDHTTKPPGGQVSTKPPAVT  119
Q8MI69|WFDC2_PIG    KCCKAGCVTICQMPN---------------------------------------------   73
                    *** ***  :.*  **

Q14508|WFDC2_HUMAN  -------DKEGSCPQVNINFPQLGLCRDQCQVDSQCPGQMKCCRNGCGKVSCVTPNF    124
Q28894|WFDC2_CANLF  -------EKEGSCPQVNTDFPQLGLCQDQCQVDSHCPGLLKCCYNGCGKVSCVTPIF    124
Q28631|WFDC2_RABIT  -------EKEGSCPS--IDFPQLGICQDLCQVDSQCPGKMKCCLNGCGKVSCVTPNF    123
Q8CHN3|WFDC2_RAT    KEG-GNGEKQGTCPS--VDFPKLGLCEDQCQMDSQCSGNMKCCRNGCGKMGCTTPKF    168
Q9DAU7|WFDC2_MOUSE  REGLGVREKQGTCPS--VDIPKLGLCEDQCQVDSQCSGNMKCCRNGCGKMACTTPKF    174
Q8MI69|WFDC2_PIG    -------EKEGSCPQVDIAFPQLGLCLDQCQVDSQCPGQLKCCRNGCGKVSCVTPVF    123
                          :*:*:**.      :*:**:*  *  **:**:* *  :*** *****: .*.** *
```

The terms "peptidomimetic" and "mimetic" refer to a synthetic chemical compound that has substantially the same functional characteristics of a naturally or non-naturally occurring polypeptide, but different (though typically similar) structural characteristics. Peptide analogs are commonly used in the field as non-peptide active compounds (e.g., drugs) with properties analogous to those of a template peptide. Such non-peptide compounds are termed "peptide mimetics" or "peptidomimetics" (Fauchere, J. Adv. Drug Res. 15:29 (1986); Veber and Freidinger TINS p. 392 (1985); and Evans et al. J. Med. Chem. 30:1229 (1987)). Peptide mimetics that are structurally similar to therapeutically useful peptides may be used to produce an equivalent or enhanced therapeutic or prophylactic effect. Generally, peptidomimetics are structurally similar to a paradigm polypeptide (i.e., a polypeptide that has a biological or pharmacological activity), such as found in a polypeptide of interest, but have one or more peptide linkages optionally replaced by a linkage selected from the group consisting of, e.g., —CH2NH—, —CH2S—, —CH2-CH2-, —CH=CH— (cis and trans), —COCH2-, —CH(OH) CH2-, and —CH2SO—. A mimetic can be either entirely composed of synthetic, non-natural analogues of amino acids, or, is a chimeric molecule of partly natural peptide amino acids and partly non-natural analogs of amino acids. A mimetic can also incorporate any amount of natural amino acid conservative substitutions as long as such substitutions also do not substantially alter the mimetic's structure and/or activity. For example, a mimetic composition is within the scope described here if it is capable of the acute kidney injury-ameliorating activity of a WFDC2 polypeptide.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymers.

The term "amino acid" refers to naturally occurring and synthetic amino acids, as well as amino acid analogs and amino acid mimetics that function in a manner similar to naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Naturally encoded amino acids are the 20 common amino acids (alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine) as well as pyrrolysine, pyrroline-carboxy-lysine, and selenocysteine.

The term "conservative amino acid substitutions" refers to the substitution (conceptually or otherwise) of an amino acid from one such group with a different amino acid from the same group. One example of substitutions is based on analyzing the normalized frequencies of amino acid changes between corresponding proteins of homologous organisms (see, e.g., Schulz, G. E. and R. H. Schirmer, Principles of Protein Structure, Springer-Verlag). According to such analyses, groups of amino acids may be defined where amino acids within a group exchange preferentially with each other and, therefore, resemble each other most in their impact on the overall protein structure (see, e.g., Schulz, G. E. and R. H. Schirmer, Principles of Protein Structure, Springer-Verlag). One example of a set of amino acid groups defined in this manner include: (i) a charged group, consisting of Glu and Asp, Lys, Arg and His; (ii) a positively-charged group, consisting of Lys, Arg and His; (iii) a negatively-charged group, consisting of Glu and Asp; (iv) an aromatic group, consisting of Phe, Tyr and Trp; (v) a nitrogen ring group, consisting of His and Trp; (vi) a large aliphatic nonpolar group, consisting of Val, Leu and Ile; (vii) a slightly-polar group, consisting of Met and Cys; (viii) a small-residue group, consisting of Ser, Ihr, Asp, Asn, Gly, Ala, Glu, Gln and Pro; (ix) an aliphatic group consisting of Val, Leu, Ile, Met and Cys; and (x) a small hydroxyl group consisting of Ser and Thr. Other examples of conservative substitutions based on shared physical properties are the substitutions within the following groups: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)).

"Percentage of sequence identity" is determined by comparing two optimally aligned sequences over a comparison window, wherein the portion of the amino acid sequence or polynucleotide sequence in the comparison window may comprise additions or deletions (i.e., gaps) as compared to the reference sequence (e.g., SEQ ID NO:1), which does not comprise additions or deletions, for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The terms "identical" or percent "identity," in the context of two or more nucleic acids or polypeptide sequences, refer to two or more sequences or subsequences that are the same sequences. Two sequences are "substantially identical" if two sequences have a specified percentage of amino acid residues or nucleotides that are the same (i.e., 95% identity, optionally 96%, 97%, 98%, or 99% identity over a specified region, or, when not specified, over the entire sequence), when compared and aligned for maximum correspondence over a comparison window, or designated region as measured using one of the following sequence comparison algorithms or by manual alignment and visual inspection. For an amino acid sequence, optionally, identity exists over a region that is at least about 50 amino acids in length, or more preferably over a region that is 100 to 150 or 200 or more amino acids in length, or where not indicated over the entire length of the reference sequence.

For sequence comparison, typically one sequence acts as a reference sequence to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 50 to 600, usually about 75 to about 200, more usually about 100 to about 150 in which a sequence may be compared to a reference sequence of the same number of contiguous positions after the two sequences are optimally aligned. Methods of alignment of sequences for comparison are well known in the art.

An algorithm for determining percent sequence identity and sequence similarity is the BLAST 2.0 algorithms, e.g., as described in, and Altschul et al. (1990) J. Mol. Biol. 215:403-410 (see also Altschul et al. (1977) Nuc. Acids Res. 25:3389-3402). Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff and Henikoff (1989) Proc. Natl. Acad. Sci. USA 89:10915) alignments (B) of 50, expectation (E) of 10, M=5, and N=−4.

The term "isolated," when applied to a nucleic acid or protein, denotes that the nucleic acid or protein is purified to be essentially free of other cellular components with which it is associated in the natural state. It is often in a homogeneous or nearly homogeneous state. It can be in either a dry or aqueous solution. Purity and homogeneity may be determined using analytical chemistry techniques known and used typically in the art, e.g., polyacrylamide gel electrophoresis, high performance liquid chromatography, etc. A protein that is the predominant species present in a preparation is substantially purified. The term "purified" in some embodiments denotes that a protein gives rise to essentially one band in an electrophoretic gel. Typically, it means that a protein is at least 85% pure, e.g., at least 95% pure, or at least 99% pure.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all.

A polynucleotide or polypeptide sequence is "heterologous" to a cell if it originates from a different cell, or, if from the same cell, is modified from its original form. For example, when a first amino acid sequence in a protein is said to be heterologous to a second amino acid sequence in the same protein, it means that the first amino acid is from a first cell or is non-naturally-occurring whereas the second amino acid is from a second cell or is modified from its original form.

"Treating" refers to any indicia of success in the treatment or amelioration or prevention of the disease, condition, or disorder, including any objective or subjective parameter such as abatement; remission; diminishing of symptoms or making the disease condition more tolerable to the patient; slowing in the rate of degeneration or decline; or making the final point of degeneration less debilitating. The treatment or amelioration of symptoms can be based on objective or subjective parameters; including the results of an examination by a physician. Accordingly, the term "treating" includes the administration of compositions, i.e, modified T cells of the present invention, to prevent or delay, to alleviate, or to arrest or inhibit development of the symptoms or conditions associated with a disease, condition or disorder as described herein. The term "therapeutic effect" refers to the reduction, elimination, or prevention of the disease, symptoms of the disease, or side effects of the disease in the subject. "Treating" or "treatment" using the methods described herein includes preventing the onset of symptoms in a subject that can be at increased risk of a disease or disorder associated with a disease, condition or disorder as described herein, but does not yet experience or exhibit symptoms, inhibiting the symptoms of a disease or disorder (slowing or arresting its development), providing relief from the symptoms or side-effects of a disease (including palliative treatment), and relieving the symptoms of a disease (causing regression). Treatment can be prophylactic (to prevent or delay the onset of the disease, or to prevent the manifestation of clinical or subclinical symptoms thereof) or therapeutic suppression or alleviation of symptoms after the manifestation of the disease or condition. The term "treatment," as used herein, includes preventative (e.g., prophylactic), curative or palliative treatment.

As used in this specification and the appended claims, the singular forms "a," "an," and "the" include plural referents unless the context clearly dictates otherwise.

BRIEF DESCRIPTION OF THE DRAWINGS

FIG. 1A—Schematic diagram of the experimental design to study epithelial recovery. Suicider (S) when expressed in cells and induced by AP20187 can acutely trigger these cells to undergo apoptosis. Remaining cells proliferate and restore the structure of the cyst.

FIG. 1B—A mosaic cyst after induced apoptosis (suicider, expressing H2B-GFP, green) was fixed and stained with antibody GP135 against podocalyxin (pink), phalloidin against filamentous actin (F-actin, red) and DAPI (blue). Optically sectioned by spinning disk confocal microscopy. Images were volume rendered and displayed. $B^{XY}$, $B^{YZ}$ and $B^{XZ}$ are voxel slices from XY, YZ and XZ planes, respectively. Scale bar=10 µm.

FIG. 1C—A mosaic cyst 2 h after adding AP20187, was imaged live by bright-field and epifluorescence microscopy, and presented as a time-lapse series. Cell debris outside the cyst with weak green fluorescence was from apoptotic cells. Red indicates the cells in G0/G1 of the cell cycle, while green indicates cells in S/G2/M. Scale bar=10 µm.

FIG. 2A—Schematic diagram of the experimental design to identify secreted proteins in the lumen of MDCK cysts.

FIG. 2B—Mass spectrometry analysis identified peptides of Canis familiaris WFDC2 protein (SEQ ID NOS 36 and 37, respectively, in order of appearance). (PSMs indicate peptide spectrum matches; c indicates carbamidomethyl group.)

FIG. 2C—Cysts grown from MDCK cells stably expressing WFDC2-GFP after 3D culture for four days, were fixed and stained with antibody GP135 against podocalyxin (red) and DAPI (blue), and imaged by spinning disk confocal microscopy. Scale bar=10 µm.

FIG. 2D—MDCK cells stably expressing WFDC2-GFP were cultured as a 2D monolayer and imaged by spinning disk confocal microscopy. An optical section close to the bottom of the cell was used for a time-lapse series, with arrows indicating two secreting vesicles.

FIG. 2E—Sequence of the MDCK cells with its Wfdc2 gene disrupted by CRISPR/Cas9 (SEQ ID NOS 38 and 39, respectively, in order of appearance). Both alleles in KO cells have an 11 bp deletion next to the protospacer adjacent motif (in red).

FIG. 2F—Single lumen percentage of day 6 cysts, grown from cells overexpressing WFDC2-GFP, signal peptide of WFDC2 (sp) fused GFP, KO cells, KO cells rescued with WFDC2-GFP, or plain MDCK cells. ****, p<0.0001; ns, no significant difference.

FIG. 2G—Cysts, grown from Wfdc2 KO or rescue cells, after culture in 3D for 4 days, were fixed and stained with antibody GP135 against podocalyxin (red) and DAPI (blue), and imaged by epifluoresence microscopy. Scale bar=20 µm.

FIG. 2H—Cysts, grown from cells as in (F), were imaged as in (G). Focused Apical Membrane Initiation Site (AMIS) marked by podocalyxin staining was quantified and presented as scatter plot. *, p<0.05.

FIG. 3B—Comparison of Wfdc2 vs. Kim1 in adult mouse kidney after I/R injury, by in situ hybridization (ISH) separately on adjacent serial sections. Scale bar=500 µm.

FIG. 3C—Comparison of Wfdc2 expression by ISH in adult mouse kidney without or with I/R injury. Scale bar=50 µm.

FIG. 3D—For ISH slices as in (C), Wfdc2-positive renal tubules were counted and presented as scatter dots plot. Each data point represents the percentage of $Wfdc2^+$ tubules in a mouse kidney. Three separate fields in a kidney slice ISH-ed with Wfdc2 were quantified and averaged for the mouse. Dunnett's test after ANOVA were used to report: *, p<0.001; **, p<0.0001; ns, no significant difference.

FIG. 3E—Different concentrations of recombinant KIM-1 extracellular domain was added in culture medium of MDCK cells for 12 h. Expression levels of Wfdc2 were quantified by real-time PCR. Note: KIM-1 concentration detected in patient urine is about 0.3-1.5 ng/ml, which is relatively low compared with NGAL (20-90 ng/ml).

FIG. 3F—Comparison of WFDC2 expression by ISH in adult human kidney with different disease outcomes. Biopsies were prepared from patients at the time of hospital admission with AKI. Scale bar=50 µm.

FIG. 3G—For ISH slices as in (F), WFDC2$^+$ renal tubules were counted and presented as scatter dots plot. Each data point represents the percentage of WFDC2$^+$ tubules in a kidney biopsy. Three separate fields in a slice were probed, quantified and averaged for the patient. Statistical analysis reports p=0.0097 in one-way ANOVA.

FIG. 4A—Percentage of single lumen cysts at day 6, grown from unmodified MDCK cells grown with 1000 ng/ml WFDC2 or 10 ng/ml (WFDC2$^{1/100}$), or BSA. Dunnett's test after ANOVA were used to report: ****, p<0.0001.

FIG. 4B—Adult mice, after kidney I/R injury of 12 h, were injected with recombinant WFDC2 protein or BSA. After another 12 h, kidney samples were prepared for immunoblotting with indicated antibodies.

FIG. 4C—For mice as in (B), serum creatinine was measured by standard assay, and presented in scatter dots plot. Each data point represents the blood sample from a mouse with indicated treatment. Tukey's test after ANOVA were used to report: **, p<0.01; ns, no significant difference.

FIG. 4D—For mice in (B) receiving recombinant WFDC2 protein, comparison of Wfdc2 vs. Kim1 by ISH separately on adjacent serial sections.

FIG. 4E—For ISH slices as in (D), Kim1-positive area was quantified and presented as scatter dots plot. Each data point represents the percentage of Kim1$^+$ area in a mouse kidney. Three separate fields of a kidney slice ISH-ed with Kim1$^+$ were quantified and averaged for the mouse. Unpaired t test reported: **, p<0.01.

DETAILED DESCRIPTION OF THE INVENTION

Figure 1:
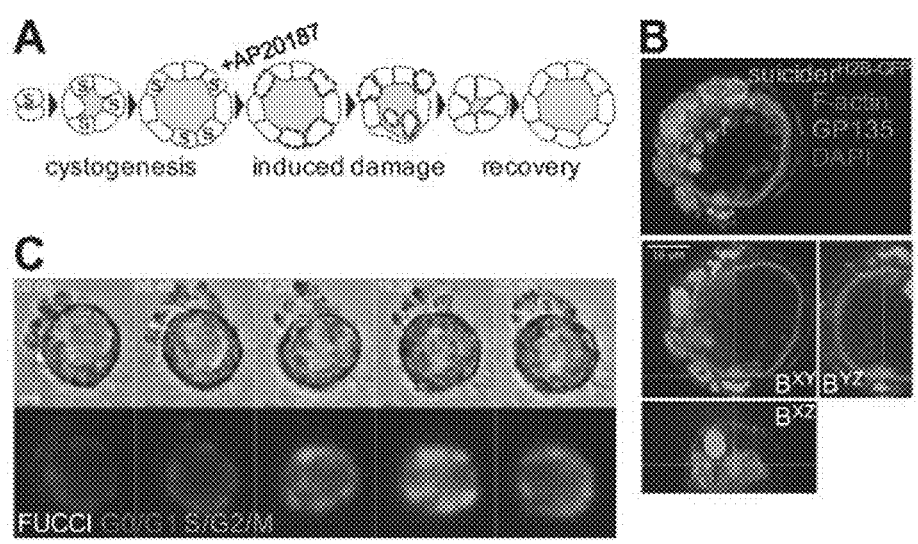
FIG. 1A-C. A 3D cell culture model of AKI

The inventors have discovered that the protein WFDC2 helps kidney cells recover from acute kidney injury (AKI). Thus, methods of treating, preventing, or ameliorating kidney injury, including but not limited to acute kidney injury, by administering WFDC2 polypeptides are provided.

Exemplary WFDC2 polypeptides include but are not limited to polypeptides having at least 70% identity, or at least 80%, 90%, 95%, 96%, 97%, 98%, 99% or 100% identity, to SEQ ID NO:1. Alternatively, active fragments of naturally-occurring WFDC2 proteins can be used, including for example, fragments that are amino or carboxyl-terminus truncations lacking, e.g., 1, 2, 3, 4, 5, or more amino acids compared to the naturally occurring protein.

The WSFD2 polypeptides can be generated by any method. For example, in some embodiments the protein can be purified from naturally-occurring sources, synthesized, or more typically can be made by recombinant production in a eukaryotic cell engineered to produce the protein. Exemplary expression systems include various yeast, insect, and mammalian expression systems.

The WFDC2 proteins as described herein can be fused to one or more fusion partners and/or heterologous amino acids to form a fusion protein. Fusion partner sequences can include, but are not limited to, amino acid tags, non-L (e.g., D-) amino acids or other amino acid mimetics to extend in vivo half-life and/or protease resistance, targeting sequences or other sequences. In some embodiments, functional variants or modified forms of the WFDC2 proteins include fusion proteins of an WFDC2 protein and one or more fusion domains. Exemplary fusion domains include, but are not limited to, polyhistidine, Glu-Glu, glutathione S transferase (GST), thioredoxin, protein A, protein G, an immunoglobulin heavy chain constant region (Fc), maltose binding protein (MBP), and/or human serum albumin (HSA). A fusion domain or a fragment thereof may be selected so as to confer a desired property. For example, some fusion domains are particularly useful for isolation of the fusion proteins by affinity chromatography. For the purpose of affinity purification, relevant matrices for affinity chromatography, such as glutathione-, amylase-, and nickel- or cobalt-conjugated resins are used. Many of such matrices are available in "kit" form, such as the Pharmacia GST purification system and the QLAexpress™ system (Qiagen) useful with (HIS6 (SEQ ID NO: 7)) fusion partners. As another example, a fusion domain may be selected so as to facilitate detection of the WFDC2 proteins. Examples of such detection domains include the various fluorescent proteins (e.g., GFP) as well as "epitope tags," which are usually short peptide sequences for which a specific antibody is available. Epitope tags for which specific monoclonal antibodies are readily available include FLAG, influenza virus haemagglutinin (HA), and c-Myc tags. In some cases, the fusion domains have a protease cleavage site, such as for Factor Xa or Trombin, which allows the relevant protease to partially digest the fusion proteins and thereby liberate the recombinant proteins therefrom. The liberated proteins can then be isolated from the fusion domain by subsequent chromatographic separation. In certain embodiments, an WFDC2 protein is fused with a domain that stabilizes the WFDC2 protein in vivo (a "stabilizer" domain). By "stabilizing" is meant anything that increases the life time of the protein in the circulating blood, regardless of whether this is because of decreased destruction, decreased clearance by the kidney, or other pharmacokinetic effect. Fusions with the Fc portion of subtypes IgG1 or IgG2a immunoglobulin are known to confer desirable pharmacokinetic properties on a wide range of proteins. See, e.g., US Patent Publication No. 2014/056879. Certain mutations of these Fc portions of these IgGs confer even better pharmacokinetic properties. See, e.g., Engineered human IgG antibodies with longer serum half-lives in primates. Hinton P R, Johlfs M G, Xiong J M, Hanestad K, Ong K C, Bullock C, Keller S, Tang M T, Tso J Y, Vasquez M, Tsurushita N. *J. Biol. Chem.* 2004 Feb. 20; 279(8):6213-16; Zhou J, Johnson J E, Ghetie V, Ober R J, Ward E S. *J Mol Biol.* 2003 Sep. 26; 332(4):901-13. Likewise, fusions to human serum albumin can confer desirable properties. Other types of fusion domains that may be selected include multimerizing (e.g., dimerizing, tetramerizing) domains and functional domains (that confer an additional biological function, as desired). Fusions may be constructed such that the heterologous peptide is fused at the amino terminus of a WFDC2 polypeptide and/or at the carboxyl terminus of a WFDC2 polypeptide.

In some embodiments, the WFDC2 polypeptides as described herein will comprise at least one non-naturally encoded amino acid. In some embodiments, a polypeptide comprises 1, 2, 3, 4, or more unnatural amino acids. Methods of making and introducing a non-naturally-occurring amino acid into a protein are known. See, e.g., U.S. Pat. Nos. 7,083,970; and 7,524,647. The general principles for the production of orthogonal translation systems that are suitable for making proteins that comprise one or more desired unnatural amino acid are known in the art, as are the general methods for producing orthogonal translation systems. For example, see International Publication Numbers WO 2002/086075, entitled "METHODS AND COMPOSITION FOR THE PRODUCTION OF ORTHOGONAL tRNA-AMINOACYL-tRNA SYNTHETASE PAIRS;" WO 2002/085923, entitled "IN VIVO INCORPORATION OF UNNATURAL AMINO ACIDS;" WO 2004/094593, entitled "EXPANDING THE EUKARYOTIC GENETIC CODE;" WO 2005/019415, filed Jul. 7, 2004; WO 2005/007870, filed Jul. 7, 2004; WO 2005/007624, filed Jul. 7, 2004; WO 2006/110182, filed Oct. 27, 2005, entitled "ORTHOGONAL TRANSLATION COMPONENTS FOR THE VIVO INCORPORATION OF UNNATURAL AMINO ACIDS" and WO 2007/103490, filed Mar. 7, 2007, entitled "SYSTEMS FOR THE EXPRESSION OF ORTHOGONAL TRANSLATION COMPONENTS IN EUBACTERIAL HOST CELLS." For discussion of orthogonal translation systems that incorporate unnatural amino acids, and methods for their production and use, see also, Wang and Schultz, (2005) "Expanding the Genetic Code." Angewandte Chemie Int Ed 44: 34-66; Xie and Schultz, (2005) "An Expanding Genetic Code." Methods 36: 227-238; Xie and Schultz, (2005) "Adding Amino Acids to the Genetic Repertoire." Curr Opinion in Chemical Biology 9: 548-554; and Wang, et al., (2006) "Expanding the Genetic Code." Annu Rev Biophys Biomol Struct 35: 225-249; Deiters, et al, (2005) "In vivo incorporation of an alkyne into proteins in *Escherichia coli*." Bioorganic & Medicinal Chemistry Letters 15:1521-1524; Chin, et al., (2002) "Addition of p-Azido-L-phenylalanine to the Genetic Code of *Escherichia coli*." J Am Chem Soc 124: 9026-9027; and International Publication No. WO2006/034332, filed on Sep. 20, 2005. Additional details are found in U.S. Pat. Nos. 7,045,337; 7,083,970; 7,238,510; 7,129,333; 7,262,040; 7,183,082; 7,199,222; and 7,217,809.

A non-naturally encoded amino acid is typically any structure having any substituent side chain other than one used in the twenty natural amino acids. Because non-naturally encoded amino acids typically differ from the natural amino acids only in the structure of the side chain, the non-naturally encoded amino acids form amide bonds with other amino acids, including but not limited to, natural or non-naturally encoded, in the same manner in which they are formed in naturally occurring polypeptides. However, the non-naturally encoded amino acids have side chain groups that distinguish them from the natural amino acids. For example, R optionally comprises an alkyl-, aryl-, acyl-, keto-, azido-, hydroxyl-, hydrazine, cyano-, halo-, hydrazide, alkenyl, alkynl, ether, thiol, seleno-, sulfonyl-, borate, boronate, phospho, phosphono, phosphine, heterocyclic, enone, imine, aldehyde, ester, thioacid, hydroxylamine, amino group, or the like or any combination thereof. Other non-naturally occurring amino acids of interest that may be suitable for use include, but are not limited to, amino acids comprising a photoactivatable cross-linker, spin-labeled amino acids, fluorescent amino acids, metal binding amino acids, metal-containing amino acids, radioactive amino acids, amino acids with novel functional groups, amino acids that covalently or noncovalently interact with other molecules, photocaged and/or photoisomerizable amino acids, amino acids comprising biotin or a biotin analogue, glycosylated amino acids such as a sugar substituted serine, other carbohydrate modified amino acids, keto-containing amino acids, amino acids comprising polyethylene glycol or polyether, heavy atom substituted amino acids, chemically cleavable and/or photocleavable amino acids, amino acids with an elongated side chains as compared to natural amino acids, including but not limited to, polyethers or long chain hydrocarbons, including but not limited to, greater than about 5 or greater than about 10 carbons, carbon-linked sugar-containing amino acids, redox-active amino acids, amino thioacid containing amino acids, and amino acids comprising one or more toxic moiety.

Another type of modification that can optionally be introduced into the WFDC2 proteins (e.g. within the polypeptide chain or at either the N- or C-terminal), e.g., to extend in vivo half-life, is PEGylation or incorporation of long-chain polyethylene glycol polymers (PEG). Introduction of PEG or long chain polymers of PEG increases the effective molecular weight of the present polypeptides, for example, to prevent rapid filtration into the urine. In some embodiments, a Lysine residue in the WFDC2 sequence is conjugated to PEG directly or through a linker. Such linker can be, for example, a Glu residue or an acyl residue containing a thiol functional group for linkage to the appropriately modified PEG chain. An alternative method for introducing a PEG chain is to first introduce a Cys residue at the C-terminus or at solvent exposed residues such as replacements for Arg or Lys residues. This Cys residue is then site-specifically attached to a PEG chain containing, for example, a maleimide function. Methods for incorporating PEG or long chain polymers of PEG are well known in the art (described, for example, in Veronese, F. M., et al., Drug Disc. Today 10: 1451-8 (2005); Greenwald, R. B., et al., Adv. Drug Deliv. Rev. 55: 217-50 (2003); Roberts, M. J., et al., Adv. Drug Deliv. Rev., 54: 459-76 (2002)), the contents of which is incorporated herein by reference.

Another alternative approach for incorporating PEG or PEG polymers through incorporation of non-natural amino acids (as described above) can be performed with the present WFDC2 polypeptides. This approach utilizes an evolved tRNA/tRNA synthetase pair and is coded in the expression plasmid by the amber suppressor codon (Deiters, A, et al. (2004). Bio-org. Med. Chem. Lett. 14, 5743-5). For example, p-azidophenylalanine can be incorporated into the present polypeptides and then reacted with a PEG polymer having an acetylene moiety in the presence of a reducing agent and copper ions to facilitate an organic reaction known as "Huisgen [3+2]cycloaddition."

In certain embodiments, specific mutations of WFDC2 proteins can be made to alter the glycosylation of the polypeptide. Such mutations may be selected to introduce or eliminate one or more glycosylation sites, including but not limited to, O-linked or N-linked glycosylation sites. In certain embodiments, the WFDC2 proteins have glycosylation sites and patterns unaltered relative to the naturally-occurring WFDC2 proteins. In certain embodiments, a variant of WFDC2 proteins includes a glycosylation variant wherein the number and/or type of glycosylation sites have been altered relative to the naturally-occurring WFDC2 proteins. In certain embodiments, a variant of a polypeptide comprises a greater or a lesser number of N-linked glycosylation sites relative to a native polypeptide. An N-linked glycosylation site is characterized by the sequence: Asn-X-Ser or Asn-X-Thr, wherein the amino acid residue designated as X may be any amino acid residue except proline. The substitution of amino acid residues to create this sequence provides a potential new site for the addition of an N-linked carbohydrate chain. Alternatively, substitutions which eliminate this sequence will remove an existing N-linked carbohydrate chain. In certain embodiments, a rearrangement of N-linked carbohydrate chains is provided, wherein one or more N-linked glycosylation sites (typically those that are naturally occurring) are eliminated and one or more new N-linked sites are created.

Exemplary WFDC2 proteins variants include cysteine variants wherein one or more cysteine residues are deleted from or substituted for another amino acid (e.g., serine) relative to the amino acid sequence of the naturally-occurring WFDC2 proteins. In certain embodiments, cysteine variants may be useful when WFDC2 proteins must be refolded into a biologically active conformation such as after the isolation of insoluble inclusion bodies. In certain embodiments, cysteine variants have fewer cysteine residues than the native polypeptide. In certain embodiments, cysteine variants have an even number of cysteine residues to minimize interactions resulting from unpaired cysteines.

The WFDC2 proteins can be used to treat, prevent, or ameliorate acute kidney injury (AKI) or other kidney injuries or kidney diseases in a human. Additional kidney disease are described in, e.g., Oxford Textbook of Clinical Nephrology Volume 1-3 4e 4th Edition (Neil Turner, Ed.), Oxford University Press, 2015; and Brenner and Rector's The Kidney, (2 Volume Set), 10e 10th Edition (K. Skorecki et al.), Elsevier, 2015. In some embodiments, WFDC2 proteins can be used to treat, prevent, or ameliorate injury (e.g., acute injury) in other epithelial or non-epithelial tissues, including but not limited to lung, liver, and pancreas.

AKI can be categorized according to pre-renal, intrinsic and post-renal causes. See, e.g., US Patent Publication No. 2017/0267759. In some embodiments, acute kidney injury or renal failure is diagnosed when either creatinine or blood urea nitrogen tests are markedly elevated in an ill patient, especially when oliguria is present. Previous measurements of renal function may offer comparison, which is especially important if a patient is known to have chronic renal failure as well. If the cause is not apparent, a large amount of blood tests and examination of a urine specimen is typically performed to elucidate the cause of acute renal failure, medical ultrasonography of the renal tract is essential to rule out obstruction of the urinary tract.

An exemplary criterium for the diagnosis of AKI is at least one of the following: Risk: serum creatinine increased 1.5 times or urine production of less than 0.5 ml/kg body weight for 6 hours. Injury: creatinine 2.0 times OR urine production less than 0.5 ml/kg for 12 h. Failure: creatinine 3.0 times OR creatinine more than 355 µmol/l (with a rise of more than 44) or urine output below 0.3 ml/kg for 24 h. Loss: persistent AKI or complete loss of kidney function for more than four weeks. End-stage Renal Disease: complete loss of kidney function for more than three months.

A rapid increase in serum creatinine may also be an indicator for a high AKI risk following medical treatment, e.g. an impairment in renal function is indicated by an increase in serum creatinine by more than 0.5 mg/dl or more than 25% within 3 days after medication.

Kidney biopsy may be performed in the setting of acute renal failure, to provide a definitive diagnosis and sometimes an idea of the prognosis, unless the cause is clear and appropriate screening investigations are reassuringly negative.

The WFDC2 protein compositions can be administered directly to the mammalian (e.g., human) subject having or exhibiting at least one symptom of acute kidney injury using any route known in the art, including e.g., by injection (e.g., intravenous, intraperitoneal, subcutaneous, parenterally, by injection, intramuscular, or intradermal). In addition, WFDC2 protein compositions can be administered, for example, orally, inhalationally, nasally, rectally or transdermally. Methods of delivery to various epithelial tissues, including but not limited to kidney can also be found in, e.g., U.S. Pat. No. 7,404,954.

The compositions administered may further comprise a pharmaceutically acceptable carrier. Pharmaceutically acceptable carriers are determined in part by the particular composition being administered, as well as by the particular method used to administer the composition. Accordingly, there are a wide variety of suitable formulations of pharmaceutical compositions (see, e.g., Remington's Pharmaceutical Sciences, 17th ed., 1989).

Formulations suitable for administration include aqueous and non-aqueous solutions, isotonic sterile solutions, which can contain antioxidants, buffers, bacteriostats, antifungal agents and solutes that render the formulation isotonic, and aqueous and non-aqueous sterile suspensions that can include suspending agents, solubilizers, thickening agents, stabilizers, and preservatives. The formulations of compounds can be presented in unit-dose or multi-dose sealed containers, such as ampoules and vials. Solutions and suspensions can be prepared from sterile powders, granules, and tablets.

The dose administered to a patient, in the context of treating acute kidney injury should be sufficient to effect a beneficial response in the subject over time, e.g., a reduction in at least one symptom of acute kidney injury (e.g., a significant decrease of serum creatinine or urea). Other markers of acute kidney injury are descried in, e.g., US Patent Publication No. 2017/0248611. The optimal dose level for any patient will depend on a variety of factors including the efficacy of the specific modulator employed, the age, body weight, physical activity, and diet of the patient, on a possible combination with other drugs, and on the severity of the acute kidney injury. The size of the dose also will be determined by the existence, nature, and extent of any adverse side-effects that accompany the administration of a particular compound or vector in a particular subject.

In determining the effective amount of a WFDC2 protein to be administered a physician may evaluate circulating plasma levels of WFDC2 protein toxicity. The dose equivalent of an WFDC2 protein can be for example from about 1 ng/kg to 10 mg/kg for a subject. Administration can be accomplished via single or divided doses.

Also provided are methods of identifying proteins other than WFDC2 that ameliorate acute kidney injury as well as three-dimensional cell culture systems for identifying such proteins. Exemplary cell culture systems as described herein, for example, comprise kidney cell cysts characterized by a hollow lumen surrounded by a layer of polarized kidney cells. Such cell systems can be generated for example as described in Thadhani, R., Pascual, M. & Bonventre, J. V. Acute renal failure. N Engl J Med 334, 1448-1460 (1996); Bonventre, J. V. Dedifferentiation and proliferation of surviving epithelial cells in acute renal failure. J Am Soc Nephrol 14 Suppl 1, S55-61 (2003). Distinct from such cysts as have been previously described, the cysts provided herein are mosaic for (i.e., some cells have and some cells do not have) sensitivity to an agent such that when the agent is introduced, some of the cells go through apoptosis, thereby modeling kidney injury. In some embodiments, the agent is AP20187 (Ariad). In some embodiments, apoptosis is induced by inducing oligomerization of a membrane localized, truncated form of caspase 8, thereby causing damage to the cysts. In some embodiments, the cyst cells further comprise a marker indicative of cell proliferation. For example, the FUCCI fluorescent marker system (Sakaue-Sawano, A. et al., Cell 132, 487-498, doi:10.1016/j.cell.2007.12.033 (2008)) can be used to distinguish proliferating cells from resting cells in cysts following induction of apoptosis by the agent.

Methods of identifying proteins that ameliorate acute kidney injury include using the above-described three-dimensional cell culture (cyst) system to screen for proteins that have a unique expression pattern indicative of a protein therapeutic for kidney injury. For example, in some embodiments, the methods comprises screening the system for proteins that are upregulated following induction of apoptosis in the three-dimensional cysts. In some embodiments, the method comprises screening for proteins secreted into the cyst lumen following apoptosis induction.

In some embodiments, the method comprises screening for proteins encoded by mRNAs expressed with a high degree of colocalization with Umod and/or NaKATPase. Following identification of proteins meeting one or more of the criteria described above, one can further test the proteins effect on kidney injury in vivo, for example in a kidney injury animal model or in a human clinical trial.

Other proteins have been determined to have characteristics WFDC2 has that are believed to make WFDC2 and effective protein for treating kidney injury. Those characteristics include, for example:

(1) being upregulated in mouse kidney in response to AKI at early and/or late time periods, as described in Liu, J. et al., *JCI Insight* 2, doi:10.1172/jci.insight.94716 (2017);

(2) being proteins that are predicted to contain signal sequences for secretion are specifically included, as described in Nielsen H. *Methods Mol Biol* 1615:23-57. doi:10.1007/978-1-4939-7033-9_2 (2017); and (3) being proteins that contain the sequence Asparagine-X-Serine, or Aspargine-X-Threonine, where X is any amino acid (except Proline) that can often be glycosylated on the Asparagine residue (This often leads to secretion of the protein from the apical surface of polarized epithelial cells (Scheiffele P, Peranen J, Simons K. *Nature* 378(6552):96-8 (1995))).

A list of proteins meeting all of the criteria above is found in the two tables (Table A and B) directly below. These proteins can be used for treating AKI as described herein for WFDC2. Accordingly, in some embodiments, a method of treating acute kidney injury in a human is provided wherein the method comprises administering to the human a sufficient amount of a polypeptide comprising an amino acid sequence at least 70% (or 80%, 90%, 95%, 99% or 100%) identical to a protein of Table A or Table B, or an active fragment thereof, to reduce at least one symptom of the acute kidney injury

TABLE A

| Protein Name | Protein ID |
|---|---|
| 11-cis retinol dehydrogenase | O55240.1 |
| 72 kDa type IV collagenase | P33434.1 |
| A disintegrin and metalloproteinase with thrombospondin motifs 1 | P97857.4 |
| A disintegrin and metalloproteinase with thrombospondin motifs 12 | Q811B3.2 |
| A disintegrin and metalloproteinase with thrombospondin motifs 16 | Q69Z28.2 |
| A disintegrin and metalloproteinase with thrombospondin motifs 2 | Q8C9W3.2 |
| A disintegrin and metalloproteinase with thrombospondin motifs 4 | Q8BNJ2.2 |
| A disintegrin and metalloproteinase with thrombospondin motifs 7 | Q68SA9.3 |
| Acid sphingomyelinase-like phosphodiesterase 3b | P58242.1 |
| ADAMTS-like protein 4 | Q80T21.1 |
| Adhesion G protein-coupled receptor E1 | Q61549.1 |
| Afamin | O89020.2 |
| Alpha-1-acid glycoprotein 2 | P07361.1 |
| Alpha-1-antitrypsin 1-1 | P07758.4 |
| Alpha-1-antitrypsin 1-4 | Q00897.1 |
| Apolipoprotein D | P51910.1 |
| Beta-2-glycoprotein 1 | Q01339.1 |
| Beta-nerve growth factor | P01139.2 |

TABLE A-continued

| Protein Name | Protein ID |
|---|---|
| Biglycan | P28653.1 |
| Bone morphogenetic protein 1 | P98063.2 |
| Bone morphogenetic protein 2 | P21274.3 |
| Calcium-activated chloride channel regulator 3A-1 | Q9QX15.1 |
| Carbonic anhydrase 14 | Q9WVT6.1 |
| Carbonic anhydrase 4 | Q64444.1 |
| Carboxylesterase 1D | Q8VCT4.1 |
| Carboxylesterase 1F | Q91WU0.1 |
| Carboxypeptidase B2 | Q9JHH6.1 |
| Carboxypeptidase E | Q00493.2 |
| Carboxypeptidase Z | Q8R4V4.2 |
| Cardiotrophin-like cytokine factor 1 | Q9QZM3.1 |
| Cathepsin E | P70269.2 |
| Cathepsin K | P55097.2 |
| Cathepsin S | O70370.2 |
| Cathepsin W | P56203.2 |
| C—C motif chemokine 2 | P10148.1 |
| C—C motif chemokine 28 | Q9JIL2.1 |
| C—C motif chemokine 7 | Q03366.1 |
| CD180 antigen | Q62192.2 |
| CD48 antigen | P18181.1 |
| CD83 antigen | O88324.1 |
| Cell migration-inducing and hyaluronan-binding protein | Q8BI06.4 |
| Ceruloplasmin | Q61147.2 |
| Chordin-like protein 1 | Q920C1.1 |
| Clusterin | Q06890.1 |
| Coagulation factor VII | P70375.1 |
| Cochlin | Q62507.2 |
| Coiled-coil domain-containing protein 80 | Q8R2G6.2 |
| Coiled-coil domain-containing protein 88B | Q4QRL3.2 |
| Collagen alpha-1(I) chain | P11087.4 |
| Collagen alpha-1(III) chain | P08121.4 |
| Collagen alpha-1(IV) chain | P02463.4 |
| Collagen alpha-1(V) chain | O88207.2 |
| Collagen alpha-1(VI) chain | Q04857.1 |
| Collagen alpha-1(XII) chain | Q60847.3 |
| Collagen alpha-1(XV) chain | O35206.2 |
| Collagen alpha-2(I) chain | Q01149.2 |
| Collagen alpha-2(VI) chain | Q02788.3 |
| Collagen alpha-4(VI) chain | A2AX52.2 |
| Collagen and calcium-binding EGF domain-containing protein 1 | Q3MI99.2 |
| Collagen triple helix repeat-containing protein 1 | Q9D1D6.2 |
| Complement C1q subcomponent subunit A | P98086.2 |
| Complement C1q tumor necrosis factor-related protein 6 | Q6IR41.1 |
| Complement C1r-A subcomponent | Q8CG16.1 |
| Complement C3 | P01027.3 |
| Complement C4-B | P01029.3 |
| Complement component C8 alpha chain | Q8K182.1 |
| Complement factor H | P06909.2 |
| Complement factor I | Q61129.3 |
| Contactin-1 | P12960.1 |
| Corticosteroid-binding globulin | Q06770.1 |
| C-X-C motif chemokine 9 | P18340.2 |
| Cysteine-rich secretory protein 1 | Q03401.1 |
| Cysteine-rich secretory protein LCCL domain-containing 2 | Q8BZQ2.1 |
| Cytokine receptor-like factor 1 | Q9JM58.1 |
| D-aspartate oxidase | Q922Z0.1 |
| Decorin | P28654.1 |
| Deoxyribonuclease-1 | P49183.2 |
| Dickkopf-related protein 3 | Q9QUN9.1 |
| Dipeptidase 2 | Q8C255.1 |
| Dipeptidyl peptidase 1 | P97821.1 |
| Ecto-ADP-ribosyltransferase 4 | Q9CRA0.1 |
| EGF-containing fibulin-like extracellular matrix protein 2 | Q9WVJ9.1 |
| EMILIN-1 | Q99K41.1 |
| EMILIN-2 | Q8K482.1 |
| Eosinophil cationic protein 2 | P97425.1 |
| Ephrin-A2 | P52801.1 |
| Epidermal growth factor-like protein 6 | Q9JJZ5.1 |
| Extracellular sulfatase Sulf-1 | Q8K007.1 |
| Fibrillin-1 | Q61554.2 |
| Fibrinogen alpha chain | E9PV24.1 |
| Fibrinogen beta chain | Q8K0E8.1 |
| Fibrinogen gamma chain | Q8VCM7.1 |
| Fibroblast growth factor 18 | O89101.1 |
| Fibroleukin | P12804.1 |
| Fibromodulin | P50608.1 |
| Fibronectin | P11276.4 |
| Fibulin-1 | Q08879.2 |
| Follistatin-related protein 1 | Q62356.2 |
| FRAS1-related extracellular matrix protein 1 | Q684R7.1 |
| Galactosylgalactosylxylosylprotein 3-beta-glucuronosyltransferase 2 | P59270.1 |
| Gastrin-releasing peptide | Q8R1I2.1 |
| Glia-derived nexin | Q07235.2 |
| Glioma pathogenesis-related protein 1 | Q9CWG1.1 |
| Glucoside xylosyltransferase 2 | Q810K9.1 |
| Glutathione peroxidase 6 | Q91WR8.2 |
| Glypican-3 | Q8CFZ4.1 |
| Gremlin-1 | O70326.1 |
| Group IID secretory phospholipase A2 | Q9WVF6.1 |
| Growth/differentiation factor 15 | Q9Z0J7.2 |
| Haptoglobin | Q61646.1 |
| Hemicentin-1 | D3YXG0.1 |
| Hemicentin-2 | A2AJ76.1 |
| Heparanase | Q6YGZ1.3 |
| IgLON family member 5 | Q8HW98.2 |
| Immunoglobulin J chain | P01592.4 |
| Immunoglobulin superfamily containing leucine-rich repeat protein | Q6GU68.1 |
| Immunoglobulin superfamily member 10 | Q3V1M1.2 |
| Inactive glycosyltransferase 25 family member 3 | A3KGW5.1 |
| Inhibin beta A chain | Q04998.1 |
| Inhibin beta B chain | Q04999.4 |
| Insulin receptor-related protein | Q9WTL4.2 |
| Inter-alpha-trypsin inhibitor heavy chain H1 | Q61702.2 |
| Inter-alpha-trypsin inhibitor heavy chain H3 | Q61704.3 |
| Interleukin-1 receptor antagonist protein | P25085.1 |
| Interleukin-1 receptor-associated kinase 3 | Q8K4B2.2 |
| Interleukin-21 receptor | Q9JHX3.1 |
| Interleukin-27 receptor subunit alpha | O70394.2 |
| Interleukin-27 subunit beta | O35228.1 |
| Kallikrein 1-related peptidase b27 | Q9JM71.1 |
| Kallikrein 1-related peptidase b3 | P00756.1 |
| Kallikrein 1-related peptidase-like b4 | P00757.1 |
| Kininogen-1 | O08677.1 |
| Leucine-rich repeat LGI family member 2 | Q8K4Z0.1 |
| Leucine-rich repeat-containing protein 66 | Q8K0B3.1 |
| Leukemia inhibitory factor | P09056.1 |
| Leukotriene-B(4) omega-hydroxylase 2 | Q99N16.2 |
| Linker for activation of T-cells family member 2 | Q9JHL0.1 |
| Lipopolysaccharide-binding protein | Q61805.2 |
| Lumican | P51885.2 |
| Ly6/PLAUR domain-containing protein 3 | Q91YK8.1 |
| Lymphocyte antigen 86 | O88188.1 |
| Lysozyme C-1 | P17897.1 |
| Lysozyme C-2 | P08905.2 |
| Lysyl oxidase homolog 2 | P58022.2 |
| Lysyl oxidase homolog 3 | Q9Z175.2 |
| Lysyl oxidase homolog 4 | Q924C6.2 |
| Macrophage metalloelastase | P34960.3 |
| Matrix metalloproteinase-19 | Q9JHI0.1 |
| Matrix metalloproteinase-9 | P41245.2 |
| Melanotransferrin | Q9R0R1.1 |
| Mesothelin | Q61468.1 |
| Microfibril-associated glycoprotein 4 | Q9D1H9.1 |
| Microfibrillar-associated protein 5 | Q9QZJ6.1 |
| Monocyte differentiation antigen CD14 | P10810.1 |
| N-acetyllactosaminide beta-1,3-N-acetylglucosaminyltransferase 3 | Q5JCS9.1 |
| N-acetylmuramoyl-L-alanine amidase | Q8VCS0.1 |
| Napsin-A | O09043.1 |
| Nephrocan | Q9CQ76.1 |
| Neuroblastoma suppressor of tumorigenicity 1 | Q61477.2 |
| Neuronal acetylcholine receptor subunit alpha-4 | O70174.2 |
| Neuronal growth regulator 1 | Q80Z24.1 |
| Neuronal pentraxin-2 | O70340.1 |
| Neurotrimin | Q99PJ0.2 |
| Neurotrophin-4 | Q8OVU4.1 |
| Neutrophil collagenase | O70138.2 |
| N-fatty-acyl-amino acid synthase/hydrolase PM20D1 | Q8C165.1 |
| Olfactomedin-like protein 2B | Q3V1G4.2 |

TABLE A-continued

| Protein Name | Protein ID |
| --- | --- |
| Osteomodulin | O35103.1 |
| Osteopontin | P10923.1 |
| Peptidyl-prolyl cis-trans isomerase FKBP10 | Q61576.2 |
| Peptidyl-prolyl cis-trans isomerase FKBP7 | O54998.1 |
| Phospholipid transfer protein | P55065.1 |
| Pigment epithelium-derived factor | P97298.2 |
| Placenta-expressed transcript 1 protein | Q8VEN2.1 |
| Plasma protease C1 inhibitor | P97290.3 |
| Pregnancy zone protein | Q61838.3 |
| Probable carboxypeptidase X1 | Q9Z100.2 |
| Procollagen C-endopeptidase enhancer 2 | Q8R4W6.2 |
| Proenkephalin-A | P22005.2 |
| Pro-epidermal growth factor | P01132.2 |
| Properdin | P11680.2 |
| Proprotein convertase subtilisin/kexin type 9 | Q80W65.2 |
| Protein APCDD1 | Q3U128.1 |
| Protein shisa-7 | Q8C3Q5.3 |
| Protein Wnt-10a | P70701.1 |
| Protein Wnt-2 | P21552.2 |
| Protein Z-dependent protease inhibitor | Q8R121.1 |
| Protein-lysine 6-oxidase | P28301.1 |
| Pulmonary surfactant-associated protein D | P50404.1 |
| Reticulon-4 receptor-like 2 | Q7M6Z0.1 |
| Retinol dehydrogenase 12 | Q8BYK4.1 |
| Secreted frizzled-related protein 1 | Q8C4U3.3 |
| Secreted frizzled-related sequence protein 4 | Q9Z1N6.1 |
| Secreted phosphoprotein 24 | Q8K1I3.2 |
| Serine protease HTRA3 | Q9D236.3 |
| Serpin H1 | P19324.3 |
| Sialic acid-binding Ig-like lectin 12 | Q91Y57.3 |
| Signal peptide, CUB and EGF-like domain-containing protein 1 | Q6NZL8.2 |
| Slit homolog 3 protein | Q9WVB4.2 |
| Sodium channel subunit beta-1 | P97952.1 |
| Soluble scavenger receptor cysteine-rich domain-containing protein SSC5D | Q8BV57.1 |
| SPARC-related modular calcium-binding protein 2 | Q8CD91.1 |
| Sperm acrosome-associated protein 7 | Q9D2S4.1 |
| Sperm-egg fusion protein Juno | Q9EQF4.1 |
| Spondin-1 | Q8VCC9.1 |
| Stanniocalcin-2 | O88452.1 |
| Sushi domain-containing protein 2 | Q9DBX3.1 |
| Sushi, von Willebrand factor type A, EGF and pentraxin domain-containing protein 1 | A2AVA0.1 |
| Tenascin | Q80YX1.1 |
| Tenascin-N | Q80Z71.2 |
| Testican-2 | Q9ER58.1 |
| Thrombospondin-2 | Q03350.2 |
| Thrombospondin-4 | Q9Z1T2.1 |
| Thy-1 membrane glycoprotein | P01831.1 |
| Toll-like receptor 12 | Q6QNU9.1 |
| Toll-like receptor 9 | Q9EQU3.3 |
| Transforming growth factor beta-1 | P04202.1 |
| Transforming growth factor beta-2 | P27090.2 |
| Tumor necrosis factor receptor superfamily member 23 | Q9ER63.2 |
| UDP-GlcNAc:betaGal beta-1,3-N-acetylglucosaminyltransferase 9 | Q8VI16.1 |
| Vitamin D-binding protein | P21614.2 |
| Vitamin K-dependent protein Z | Q9CQW3.1 |
| Voltage-dependent calcium channel subunit alpha-2/delta-1 | O08532.1 |
| V-type immunoglobulin domain-containing suppressor of T-cell activation | Q9D659.2 |
| WNT1-inducible-signaling pathway protein 1 | O54775.1 |
| Xaa-Pro aminopeptidase 2 | B1AVD1.1 |
| Zinc transporter ZIP8 | Q91W10.1 |
| Zinc-alpha-2-glycoprotein | Q64726.2 |

TABLE B

| Protein Name | Protein ID used during Prediction |
| --- | --- |
| pantetheinase precursor [Canis familiaris] | NP_001003372.1 |
| latent-transforming growth factor beta-binding protein 2 isoform 1 | XP_547906.3 |
| alpha-2-macroglobulin receptor-associated protein [Canis familiaris] | XP_536218.3 |
| alpha-N-acetylgalactosaminidase [Canis familiaris] | XP_538347.2 |
| beta-hexosaminidase subunit alpha isoform X1 [Canis familiaris] | XP_544758.2 |
| cathepsin B isoform X1 [Canis familiaris] | XP_543203.3 |
| C—C motif chemokine 7 precursor [Canis familiaris] | NP_001010960.1 |
| chondroitin sulfate synthase 1 [Canis familiaris] | XP_545821.3 |
| collagen alpha-1(VII) chain precursor [Canis familiaris] | NP_001002980.1 |
| complement C1r subcomponent [Canis familiaris] | XP_534901.2 |
| contactin-3 isoform X1 [Canis familiaris] | XP_533761.4 |
| deoxyribonuclease-1 precursor [Canis familiaris] | NP_001002946.1 |
| dolichyl-phosphate beta-glucosyltransferase isoform X1 [Canis familiaris] | XP_534493.2 |
| endoplasmin precursor [Canis familiaris] | NP_001003327.1 |
| extracellular matrix protein 2 isoform X1 [Canis familiaris] | XP_533562.4 |
| fibulin-5 isoform X1 [Canis familiaris] | XP_537350.3 |
| fibulin-7 isoform X2 [Canis familiaris] | XP_540177.3 |
| GDH/6PGL endoplasmic bifunctional protein isoform X2 [Canis familiaris] | XP_546762.3 |
| heparan sulfate glucosamine 3-O-sulfotransferase 1 [Canis familiaris] | XP_536238.1 |
| hepatocyte growth factor-like protein isoform X1 [Canis familiaris] | XP_541884.3 |
| high affinity cAMP-specific 3',5'-cyclic phosphodiesterase 7A [Canis familiaris] | XP_544104.2 |
| indian hedgehog protein [Canis familiaris] | XP_545653.3 |
| laminin subunit gamma-2 precursor [Canis familiaris] | NP_001003351.1 |
| leukemia inhibitory factor precursor [Canis familiaris] | NP_001184002.1 |
| lysine-specific demethylase 3B isoform X1 [Canis familiaris] | XP_531921.3 |
| lysozyme-like protein 6 [Canis familiaris] | XP_537611.4 |

TABLE B-continued

| Protein Name | Protein ID used during Prediction |
| --- | --- |
| metalloproteinase inhibitor 1 precursor [Canis familiaris] | NP_001003182.1 |
| N-sulphoglucosamine sulphohydrolase precursor [Canis familiaris] | NP_001003114.1 |
| plexin-B1 [Canis familiaris] | XP_533841.3 |
| prenylcysteine oxidase 1 [Canis familiaris] | XP_538538.2 |
| protein FAM185A [Canis familiaris] | XP_533108.3 |
| rho GTPase-activating protein 11A isoform X2 | XP_544601.4 |
| selenoprotein P precursor-U [Canis familiaris] | NP_001108590.1 |
| semaphorin-3C [Canis familiaris] | XP_533139.2 |
| stanniocalcin-1 [Canis familiaris] | XP_543238.3 |
| transforming growth factor beta-2 isoform X1 [Canis familiaris] | XP_545713.2 |
| tripeptidyl-peptidase 1 precursor [Canis familiaris] | NP_001013869.1 |
| vascular endothelial growth factor receptor 1 isoform X2 [Canis familiaris] | XP_534520.2 |
| zinc phosphodiesterase ELAC protein 2 isoform X3 [Canis familiaris] | XP_546630.2 |
| B-cell linker protein | XP_543943.2 |
| carboxypeptidase M precursor | NP_001005502.1 |
| cathepsin D | AAH57931.1 |
| D-aspartate oxidase | XP_532262.2 |
| EGF-like repeats and discoidin 1-like domains 3 | XP_546036.2 |
| FLT1 | AKI72421.1 |
| folliculin-interacting protein 2 | XP_532705.3 |
| follistatin | XP_536475.4 |
| follistatin-like 1 | AAH00055.1 |
| GDH/6PGL endoplasmic bifunctional protein isoform X2 | XP_006538525.1 |
| glucosidase 2 subunit beta isoform X2 | XP_542057.3 |
| growth/differentiation factor 11 preproprotein | NP_005802.1 |
| hyaluronan-binding protein 2 isoform 1 preproprotein | NP_004123.1 |
| kallikrein-10 isoform X1 | XP_016882482.1 |
| laminin subunit beta-1 precursor | NP_002282.2 |
| laminin subunit beta-2 | XP_533831.2 |
| lysosomal protective protein isoform a precursor | NP_000299.2 |
| neuronal pentraxin II | AAH48275.2 |
| noelin | XP_537805.3 |
| noggin precursor | NP_005441.1 |
| polyserase-2 | XP_547044.3 |
| probable ATP-dependent RNA helicase DDX17 isoform 3 | NP_001091974.1 |
| pro-neuregulin-1, membrane-bound isoform isoform GGF2 precursor | NP_039256.2 |
| protein TMEPAI isoform c precursor | NP_954640.1 |
| pyruvate dehydrogenase phosphatase regulatory subunit, mitochondrial | XP_536787.4 |
| retinol dehydrogenase 11 isoform 1 precursor | NP_057110.3 |
| semaphorin-6C isoform X8 | XP_540309.3 |
| similar to carboxylesterase 2 isoform 1 isoform 1 | XP_546889.2 |
| similar to CDK105 protein | XP_541530.1 |
| similar to Complement factor B precursor (C3/C5 convertase) (Properdin factor B) (Glycine-rich beta glycoprotein) (GBG) (PBF2) isoform 1 | XP_532086.2 |
| similar to cytosolic sialic acid 9-O-acetylesterase homolog isoform 1 | XP_546429.2 |
| similar to hypothetical protein | XP_535415.1 |
| similar to lysyl oxidase-like 3 precursor isoform 1 | XP_540217.2 |
| similar to Placenta growth factor precursor (PIGF) | XP_547910.1 |
| similar to podocan isoform 1 | XP_536704.2 |
| torsin-1B isoform X1 | XP_005251984.1 |
| tubulointerstitial nephritis antigen-like 1 | XP_535330.3 |
| unconventional myosin-Vc | XP_544680.3 |
| versican core protein isoform X4 | XP_546039.3 |

EXAMPLES

Acute kidney injury (AKI) is an enormous unmet clinical problem that occurs in 1-7% of hospitalizations and up to 58% of Intensive Care Unit admissions (ICU). Mortality can be as high as 50-70% for ICU patients with AKI [citing: Chertow, G. M., Burdick, E., Honour, M., Bonventre, J. V. & Bates, D. W. Acute kidney injury, mortality, length of stay, and costs in hospitalized patients. *J Am Soc Nephrol* 16, 3365-3370, doi:10.1681/ASN.2004090740 (2005); Liangos, O. et al. Epidemiology and outcomes of acute renal failure in hospitalized patients: a national survey. *Clin J Am Soc Nephrol* 1, 43-51, doi:10.2215/CJN.00220605 (2006); Vesconi, S. et al. Delivered dose of renal replacement therapy and mortality in critically ill patients with acute kidney injury. *Crit Care* 13, R57, doi:10.1186/cc7784 (2009)]. A 4-year survey in a tertiary hospital reported a 3% overall incidence rate of AKI, and a nearly 10-fold increase of in-hospital mortality for patients with AKI [citing: Fang, Y. et al. Acute kidney injury in a Chinese hospitalized population. *Blood Purif* 30, 120-126, doi:10.1159/000319972 (2010)]. AKI is a significant contributor to the progression of chronic kidney disease (CKD) [citing: Hsu, C. Y. Yes, AKI truly leads to CKD. *J Am Soc Nephrol* 23, 967-969, doi:10.1681/ASN.2012030222 (2012); Siew, E. D. & Deger, S. M. Recent advances in acute kidney injury epidemiology. *Curr Opin Nephrol Hypertens* 21, 309-317, doi:10.1097/MNH.0b013e3283521d95 (2012); Chawla, L. S., Eggers, P. W., Star, R. A. & Kimmel, P. L. Acute kidney injury and chronic kidney disease as interconnected syndromes. *N Engl J Med* 371, 58-66, doi:10.1056/NEJMra1214243 (2014); Ferenbach, D. A. & Bonventre, J. V. Mechanisms of maladaptive repair after AKI leading to accelerated kidney ageing and CKD. *Nat Rev Nephrol* 11, 264-276, doi:10.1038/nmeph.2015.3 (2015)]. AKI is more common in the elderly and, as the elderly population grows dramatically, treating AKI to promote patient survival and prevent progression to CKD is becoming more urgent [citing: Hsu, C. Y. et al. Nonrecovery of kidney function and death after acute on chronic renal failure. *Clin J Am Soc Nephrol* 4, 891-898, doi:10.2215/CJN.05571008 (2009); Hsu, R. K., McCulloch, C. E., Dudley, R. A., Lo, L. J. & Hsu, C. Y. Temporal changes in incidence of dialysis-requiring AKI. *J Am Soc Nephrol* 24, 37-42, doi:10.1681/ASN.2012080800 (2013)].

The causes of AKI are complex and it usually occurs secondarily to other conditions, such as sepsis, cardiovascular disease, major surgery, etc. On the cellular level, hypoxia or toxins in renal tubules induce apoptosis and/or necrosis of renal tubular epithelial cells; severe damage of these cells is the hallmark of AKI [citing: Devarajan, P. Update on mechanisms of ischemic acute kidney injury. *J Am Soc Nephrol* 17, 1503-1520, doi:10.1681/ASN.2006010017 (2006); Thadhani, R., Pascual, M. & Bonventre, J. V. Acute renal failure. *N Engl J Med* 334, 1448-1460, doi:10.1056/NEJM199605303342207 (1996)].

Despite decades of study [citing: Liu, J. et al. Molecular characterization of the transition from acute to chronic kidney injury following ischemia/reperfusion. *JCI Insight* 2, doi:10.1172/jci.insight.94716 (2017); Kumar, S. et al. Sox9 Activation Highlights a Cellular Pathway of Renal Repair in the Acutely Injured Mammalian Kidney. *Cell Rep* 12, 1325-1338, doi:10.1016/j.celrep.2015.07.034 (2015)], there is no specific therapy for AKI, only supportive care [citing: Tolwani, A. Continuous renal-replacement therapy for acute kidney injury. *N Engl J Med* 367, 2505-2514, doi:10.1056/NEJMct1206045 (2012); Tolwani, A. Continuous renal-replacement therapy for acute kidney injury. *N Engl J Med* 368, 1160-1161, doi:10.1056/NEJMc1301071 (2013)]. Recovery after AKI is driven by dedifferentiation, proliferation, and redifferentiation of the remaining tubular epithelial cells [citing: Bonventre, J. V. Dedifferentiation and proliferation of surviving epithelial cells in acute renal failure. *J Am Soc Nephrol* 14 Suppl 1, S55-61 (2003); Humphreys, B. D. et al. Repair of injured proximal tubule does not involve specialized progenitors. *Proc Natl Acad Sci USA* 108, 9226-9231, doi:10.1073/pnas.1100629108 (2011)] or progenitor cells [citing: Kang, H. M. et al. Sox9-Positive Progenitor Cells Play a Key Role in Renal Tubule Epithelial Regeneration in Mice. *Cell Rep* 14, 861-871, doi:10.1016/j.celrep.2015.12.071 (2016)], but not by stem cells from outside of the kidney [citing: Humphreys, B. D. & Bonventre, J. V. Mesenchymal stem cells in acute kidney injury. *Annu Rev Med* 59, 311-325, doi:10.1146/annurev.med.59.061506.154239 (2008)]. No intervention has been reported to promote recovery from AKI in humans.

We have developed a three-dimensional (3D) cell culture model of AKI by using mosaic cysts of the extensively-studied Madin-Darby canine kidney (MDCK) cell line and performed mRNA microarray analysis and mass spectrometry analysis of secreted proteins. We found that Wfdc2 expression is upregulated after AKI in this culture model and that upregulation of WFDC2 expression in renal biopsies from AKI patients correlates with good outcomes in AKI patients. We further observed that intravenous injection of WFDC2 protein promotes recovery of mouse kidney from experimental AKI, suggesting that WFDC2 may be a potential therapeutic for AKI.

A Cell Culture Model of AKI

We modeled AKI in vitro using MDCK cells grown as 3D cystic structures consisting of a uniform monolayer of well-polarized epithelial cells surrounding a roughly spherical liquid-filled lumen. These cysts have been widely used as a model for renal epithelial tubules.

Figure 5:
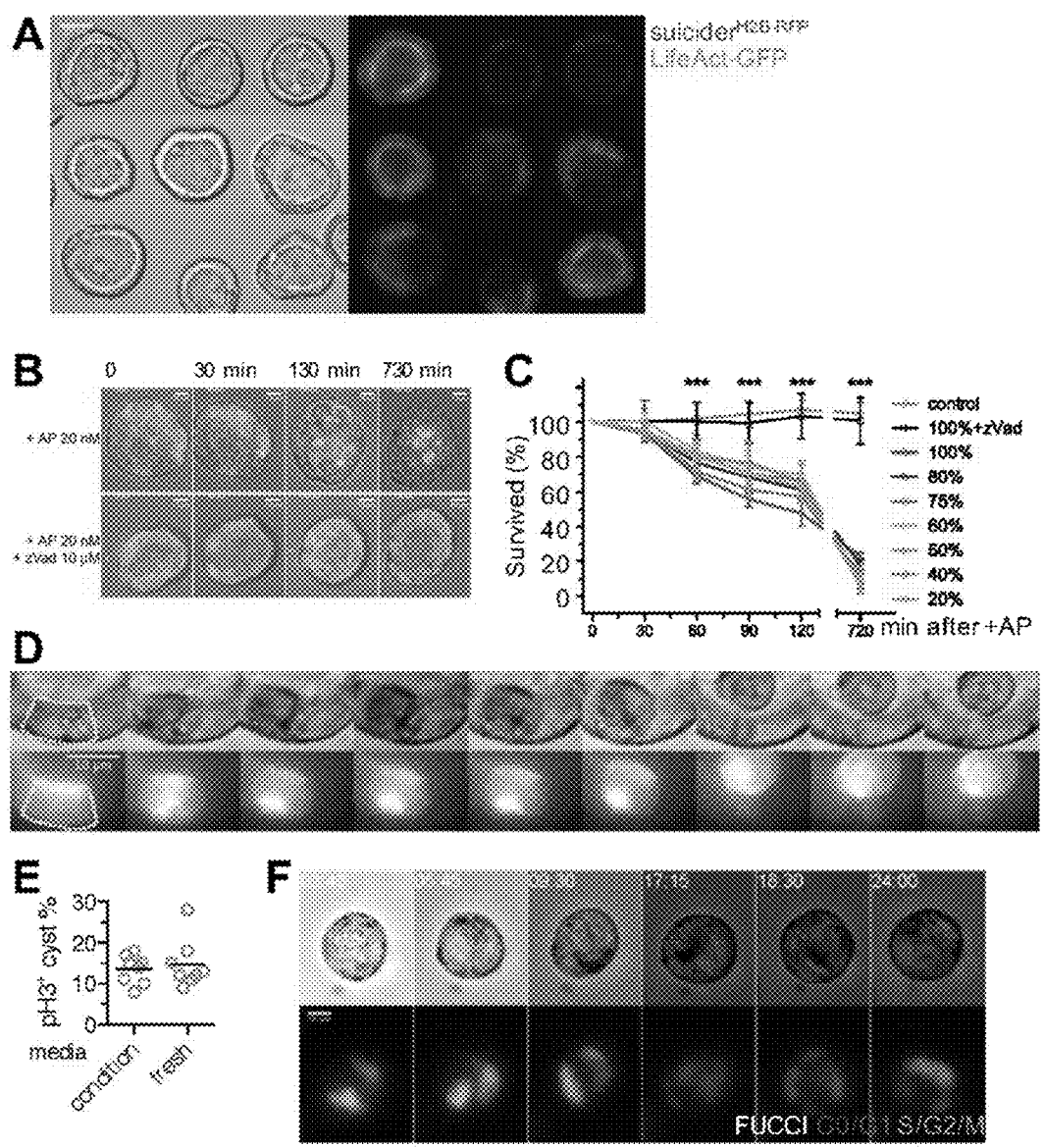
FIG. 5A—Mosaic cysts after culture in 3D for 6 days were living imaged by bright field and epifluorescence microscopy. Cysts were cropped out as 75×75 µm squares from the same field of view. Scale bar=25 µm.
FIG. 5B—Mosaic cysts after culture in 3D for 3 days were living imaged by bright field and epifluoresence microscopy. Green cells were expressing suicider. Time 0 was when 20 nM AP20187 without or with Z-VAD-FMK was added. Scale bar=10 µm.
FIG. 5C—Cells cultured as a 2D monolayer with varying percentages of cells expressing suicider were used. After induced apoptosis, cells expressing suicider remaining alive (impermeable to propidium iodide) were counted by epifluoresence microscopy.
FIG. 5D—Mosaic cysts after culture in 3D for 4 days were living imaged by bright field (top row) and epifluoresence microscopy (bottom row). Suicider cells co-expressed LifeAct-RFP. Time lapse images of a dying cell being extruded are presented, with the cell being extruded outlined by the yellow dot lines in the first frame. Scale bar=10 µm.
FIG. 5E—Madin-Darby canine kidney (MDCK) mosaic cysts with suicider expressing cells after culture in 3D for 6 days were damaged and allowed to recover for 12 h in either conditioned media or fresh media. Cells were fixed and stained with an antibody against phospho-Histone H3 (pH3) and DAPI. Images were captured by epifluoresence microscopy, quantified and presented as scatter dots plot. Each data point represents the percentage of pH3+ cysts cultured in a well. Statistical analysis reports p=0.6186 in unpaired t test.
FIG. 5F—MDCK cells expressing Fucci G0/G1$^{red}$ S/G2/M$^{green}$ after culture in 3D for 12 h were living imaged by bright field (top row) and epifluoresence (bottom row) microscopy, and presented as a time-lapse montage. Scale bar=10 µm.

We constructed mosaic cysts (FIG. 5A) in which some cells were sensitive to a small molecule (AP20187, Ariad) that could induce apoptosis by oligomerization of a membrane-localized, truncated form of caspase 8 and thereby cause damage to the cysts (FIGS. 5A-B, 5*d*). Apoptosis-induced damage was specific in that treating cells with the general caspase inhibitor Z-VAD-FMK completely protected the cysts from damage (FIGS. 5B-C). Intriguingly, the remaining cells in the damaged cysts were able to re-enter the cell cycle and restore the cysts to their pre-apoptotic state (FIGS. 1C, 5E).

We used the FUCCI fluorescent marker system [citing: Sakaue-Sawano, A. et al. Visualizing spatiotemporal dynamics of multicellular cell-cycle progression. *Cell* 132, 487-498, doi:10.1016/j.cell.2007.12.033 (2008)] to distinguish proliferating cells from resting cells in recovering cysts (FIGS. 1C, 5F). Next, we performed differential gene expression analysis to compare proliferating versus non-proliferating cells. A variety of genes were identified that have a broad range of cellular functions (Suppl. Table 2). Using this model of AKI, we have generated a list of gene candidates that might be important for renal injury recovery in vivo.

WFDC2 is a Secreted Protein

Figure 2:
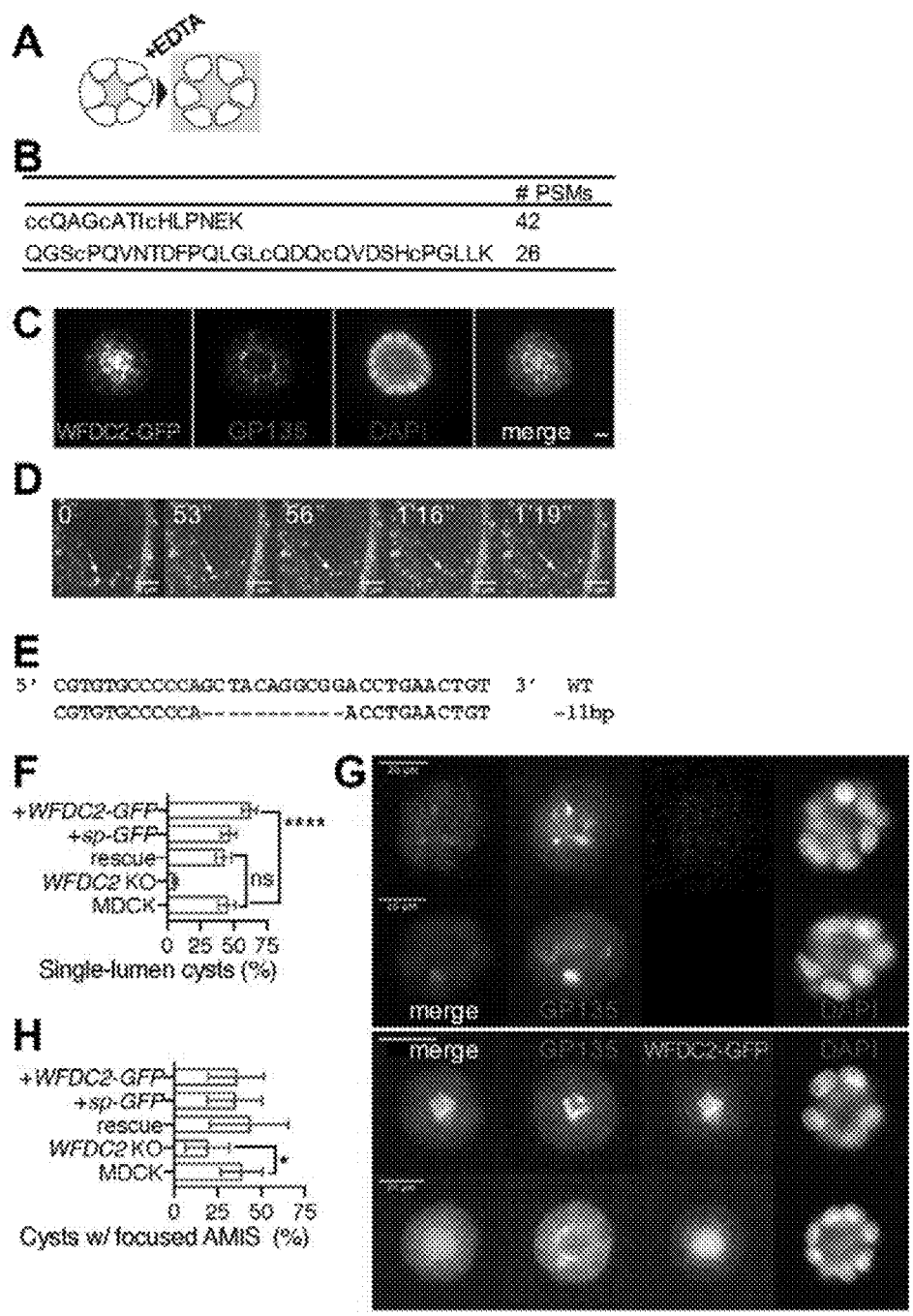
FIG. 2A-H. WFDC2 is a secreted protein

Like all epithelia, renal epithelial cells exhibit polarized secretion. Although MDCK cysts have been widely used as a model of renal tubules [citing: Bryant, D. M. & Mostov, K. E. From cells to organs: building polarized tissue. *Nat Rev Mol Cell Biol* 9, 887-901, doi:10.1038/nrm2523 (2008); Roman-Femandez, A. & Bryant, D. M. Complex Polarity: Building Multicellular Tissues Through Apical Membrane Traffic. *Traffic* 17, 1244-1261, doi:10.1111/tra.12417 (2016); 24 Bemascone, I., Hachimi, M. & Martin-Belmonte, F. Signaling Networks in Epithelial Tube Formation. *Cold Spring Harb Perspect Biol*, doi:10.1101/cshperspect.a027946 (2017)], we are unaware of a report of the profiling of the apically secreted proteins from developing cysts. We used EDTA solution to disassemble the cysts and performed proteomics analysis of secreted proteins from the liquid in the cyst lumen (FIG. 2A).

Figure 6:
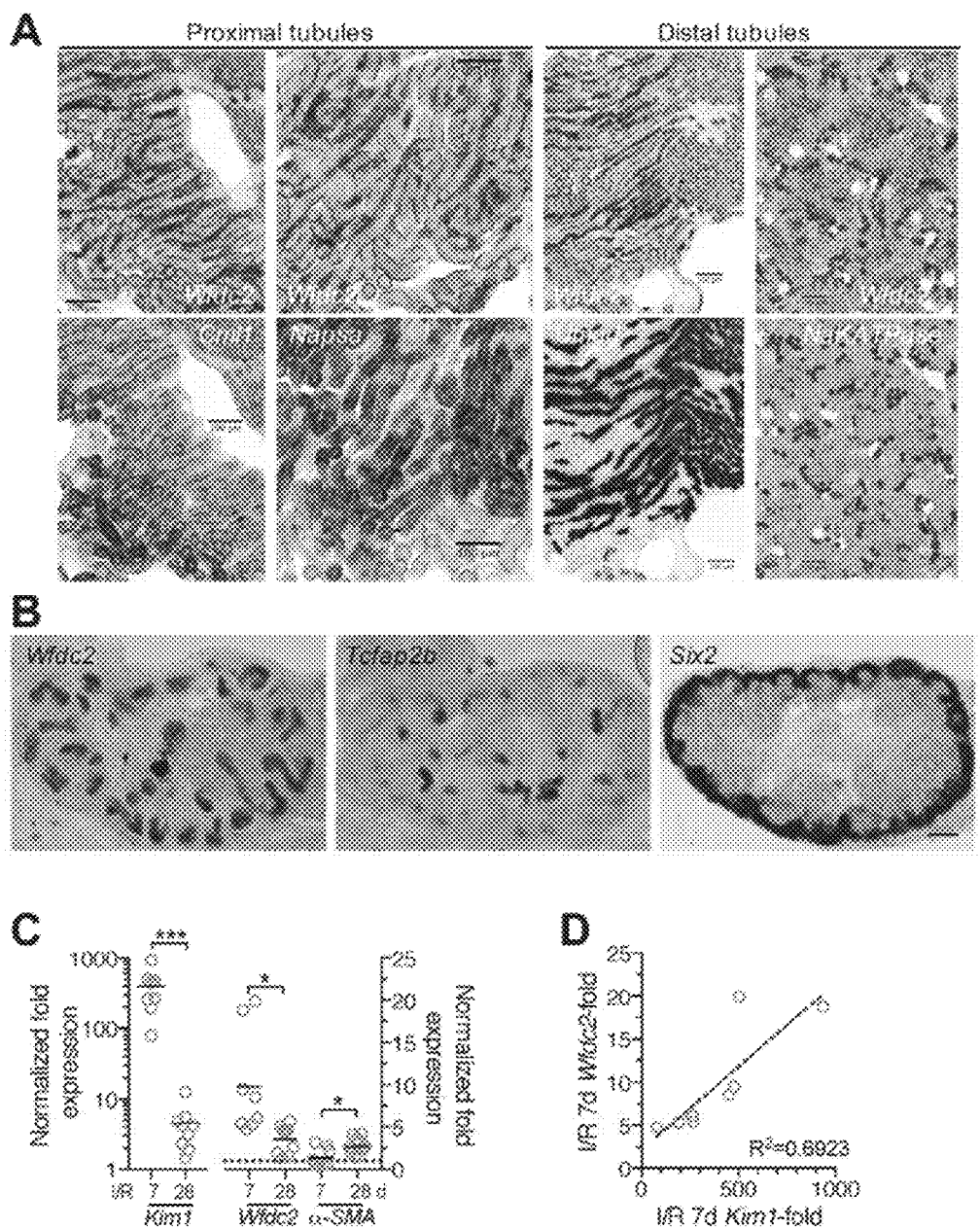
FIG. 6A—Comparison of Wfdc2 vs. Cml1, Napsa, Umod or NaKATPase expression by ISH separately on adjacent serial sections of adult mouse kidney. Scale bar=100 µm.
FIG. 6B—Comparison of Wfdc2 vs. Tcfap2b and Six2 expression by ISH separately on adjacent serial sections of embryo mouse kidney (E13.5). Scale bar=100 µm.
FIG. 6C—Normalized expression levels of Wfdc2, Kim1 and α-smooth muscle actin (α-SMA) (a myofibroblast marker) in adult mouse kidney at 7 or 28 days (d) after I/R injury were quantified by real-time PCR. Each data point represents the average of triplicate measurements of one mouse. Overall, the data showed that the kidneys tended to return to a non-myofibroblast, non-mesenchymal state by 28 d post I/R injury.
FIG. 6D—The 7d post I/R normalized expression data for Kim1 and Wfdc2 from S3C were highly variable. Each data point was plotted with normalized expression of Kim1 on the x-axis and normalized expression of Wfdc2 on the y-axis. A best-fit line was drawn with correlation coefficient of $R^2$=0.6923.

Wfdc2 was highly expressed in recovering cysts (Suppl. Table 2). The protein WFDC2 was identified in our mass spectrometry analysis of the liquid in the cyst lumen (FIG. 2B). Using a C-terminal GFP fusion protein and live imaging, we confirmed that WFDC2 is secreted into the lumen (FIG. 2C-D). In adult mouse kidney, Wfdc2 is expressed in tubular structures, with high expression in distal tubules marked by expression of Umod and NaKATPase (FIG. 6. In embryonic kidney, Wfdc2 is expressed in patches, with minimal colocalization with either Six2 or Tcfap2b (FIG. 6).

Figure 4:
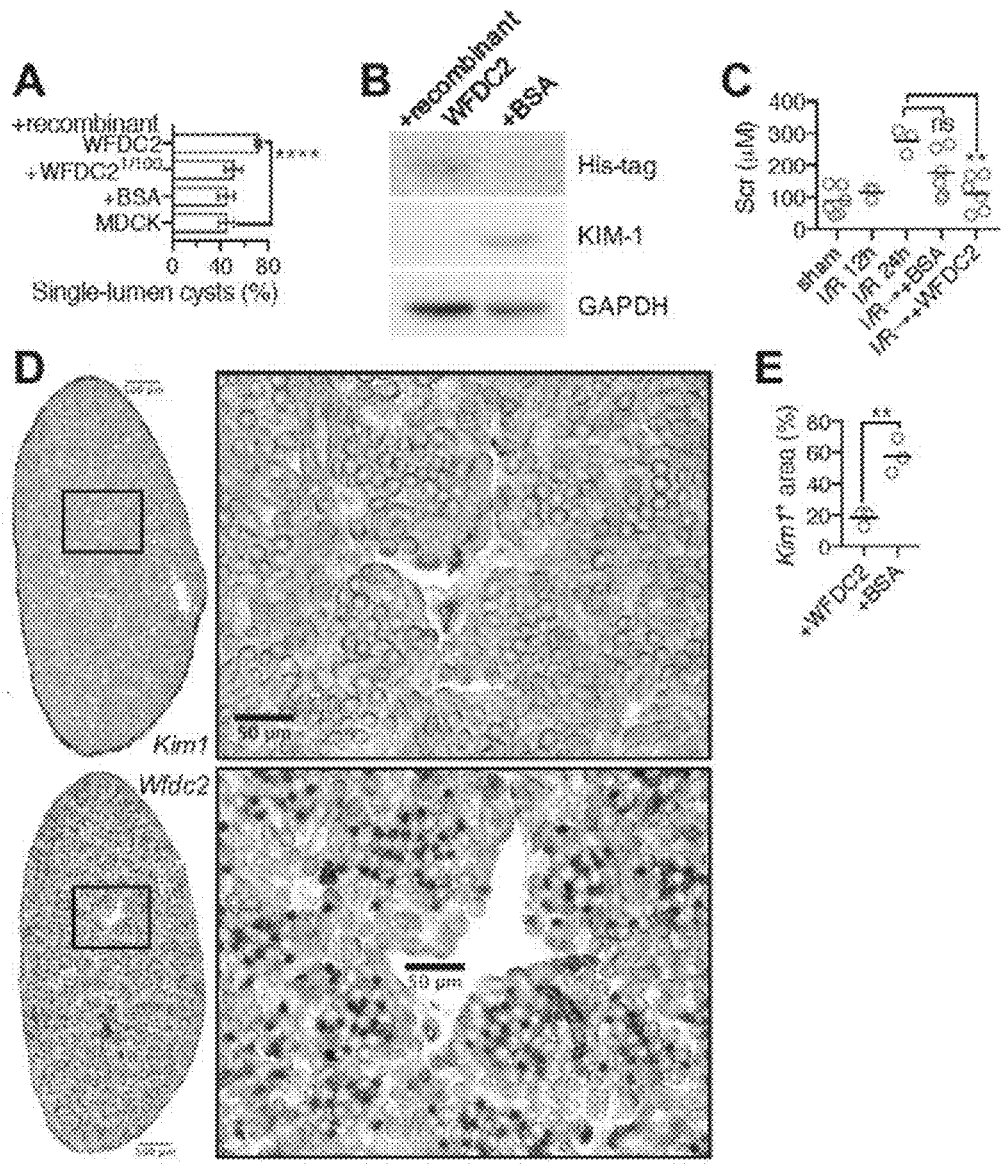
FIG. 4A-E. Secreted WFDC2 promotes renal recovery after AKI

To study the cellular function of Wfdc2, we analyzed lumen formation in the 3D culture model. We found that overexpression of Wfdc2 increased the percentage of single lumen cysts (FIG. 2F), an indicator of enhanced polarized secretion [citing: Bryant, D. M. et al. A molecular switch for the orientation of epithelial cell polarization. *Dev Cell* 31, 171-187, doi:10.1016/j.devcel.2014.08.027 (2014)]. We disrupted Wfdc2 by CRISPR/Cas9 (FIG. 2E) and found that apical surface proteins were mislocalized in cysts lacking Wfdc2 (FIG. 2G-H), along with an increased percentage of multi-lumen cysts in later cystogenesis (FIG. 2F). Conversely, adding recombinant WFDC2 protein to the culture medium enhanced single lumen formation (FIG. 4A). Thus, injury-induced extracellular WFDC2 could promote cystogenesis by enhanced epithelial polarization.

Figure 3:
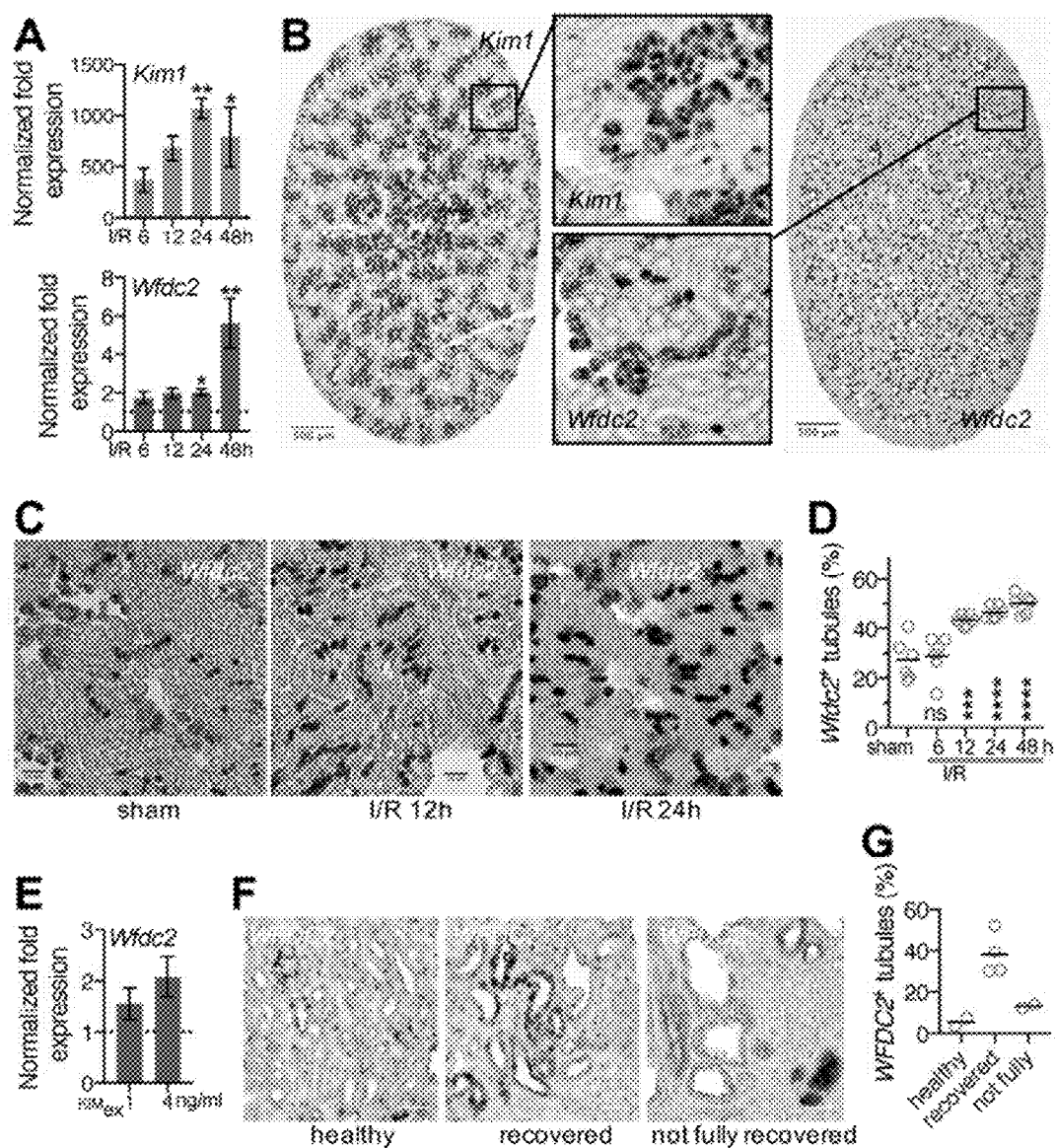
FIG. 3A-G. Upregulation of Wfdc2 after AKI, and correlates with good prognosis of patients FIG. 3A—Expression levels of Wfdc2 and Kim1 in adult mouse kidney after ischemic/reperfusion (I/R) injury were quantified by real-time PCR. Dunnett's test after ANOVA were used to report: *, p<0.05, **, p<0.01.

Upregulation of Wfdc2 after a Mouse Model of AKI and Correlation with Patient Outcome We employed a mouse model of AKI to further analyze the role of Wfdc2 in kidney injury recovery [citing: Wei, Q. & Dong, Z. Mouse model of ischemic acute kidney injury: technical notes and tricks. *Am J Physiol Renal Physiol* 303, F1487-1494, doi:10.1152/ajprenal.00352.2012 (2012); Xu, X. et al. Delayed ischemic preconditioning contributes to renal protection by upregulation of miR-21. *Kidney Int* 82, 1167-1175, doi:10.1038/ki.2012.241 (2012)]. Although there are limitations, the widely used ischemia/reperfusion (I/R) protocol damages kidney in several ways that are similar to AKI in humans [citing: Wei, Q. & Dong, Z. Mouse model of ischemic acute kidney injury: technical notes and tricks. *Am J Physiol Renal Physiol* 303, F1487-1494, doi: 10.1152/ajprenal.00352.2012 (2012); Liu, K. D., Humphreys, B. D. & Endre, Z. H. The ten barriers for translation of animal data on AKI to the clinical setting. *Intensive Care Med* 43, 898-900, doi:10.1007/s00134-017-4810-4 (2017)]. Wfdc2 is upregulated in regions surrounding, but apparently not overlapping with, areas that express Kim1 (FIG. 3B), which was the first gene identified to be upregulated in AKI damaged kidneys [citing: Ichimura, T. et al. Kidney injury molecule-1 (KIM-1), a putative epithelial cell adhesion molecule containing a novel immunoglobulin domain, is upregulated in renal cells after injury. *J Biol Chem* 273, 4135-4142 (1998)]. (We also examined the localization in mouse I/R kidneys of >200 other genes that were up-regulated in our 3D culture model, but none had a similar localization pattern to Wfdc2; data not shown). Interestingly, the upregulation of Wfdc2 occurs later than Kim1 after injury (FIG. 3A). Furthermore, recombinant KIM-1 extracellular domain upregulates the expression of Wfdc2 in cell culture (FIG. 3E). KIM-1 is localized to the apical surface of damaged proximal tubule cells [citing: Kusaba, T., Lalli, M., Kramann, R, Kobayashi, A. & Humphreys, B. D. Differentiated kidney epithelial cells repair injured proximal tubule. *Proc Natl Acad Sci USA* 111, 1527-1532, doi:10.1073/pnas.1310653110 (2014)]. The extracellular domain of KIM-1 can be proteolytically shed from this surface [citing: Bonventre, J. V. Kidney injury molecule-1 (KIM-1): a urinary biomarker and much more. *Nephrol Dial Transplant* 24, 3265-3268, doi:10.1093/ndt/gfp010 (2009)], and most likely is carried by urine to the distal tubules, where it may induce the expression of Wfdc2 (FIG. 6). Although we identified apically secreted WFDC2, we cannot rule out that WFDC2 may act elsewhere, perhaps nonexclusively. That addition of WFDC2 to the outside of polarized MDCK cysts enhances single lumen cyst formation suggests that WFDC2 may act on the basolateral surface of MDCK cells and/or that this compact, relatively small protein reaches the apical surface and lumen.

We then analyzed the expression pattern of WFDC2 in kidney biopsies of patients suffering from AKI (FIG. 3F-G, Suppl. Table 1). Intriguingly, patients who had high WFDC2 expression had significantly better recovery of kidney tubule morphology (FIG. 3F-G) and renal function (Suppl. Table 1) during hospitalization, compared to patients with lower WFDC2 expression. In short, WFDC2 was up-regulated after AKI and its expression level correlated with the outcome of AKI patients. It should be noted that the serum concentration of WFDC2 has been shown to correlate with the severity of CKD and fibrosis in patients [citing: Wan, J. et al. Elevated serum concentrations of HE4 as a novel biomarker of disease severity and renal fibrosis in kidney disease. *Oncotarget* 7, 67748-67759, doi:10.18632/oncotarget.11682 (2016)]. In our murine AKI model, within 28 d of I/R injury, markers of fibrosis returned to baseline (FIG. 6).

Secreted WFDC2 Helps Renal Recovery after AKI

Figure 7:
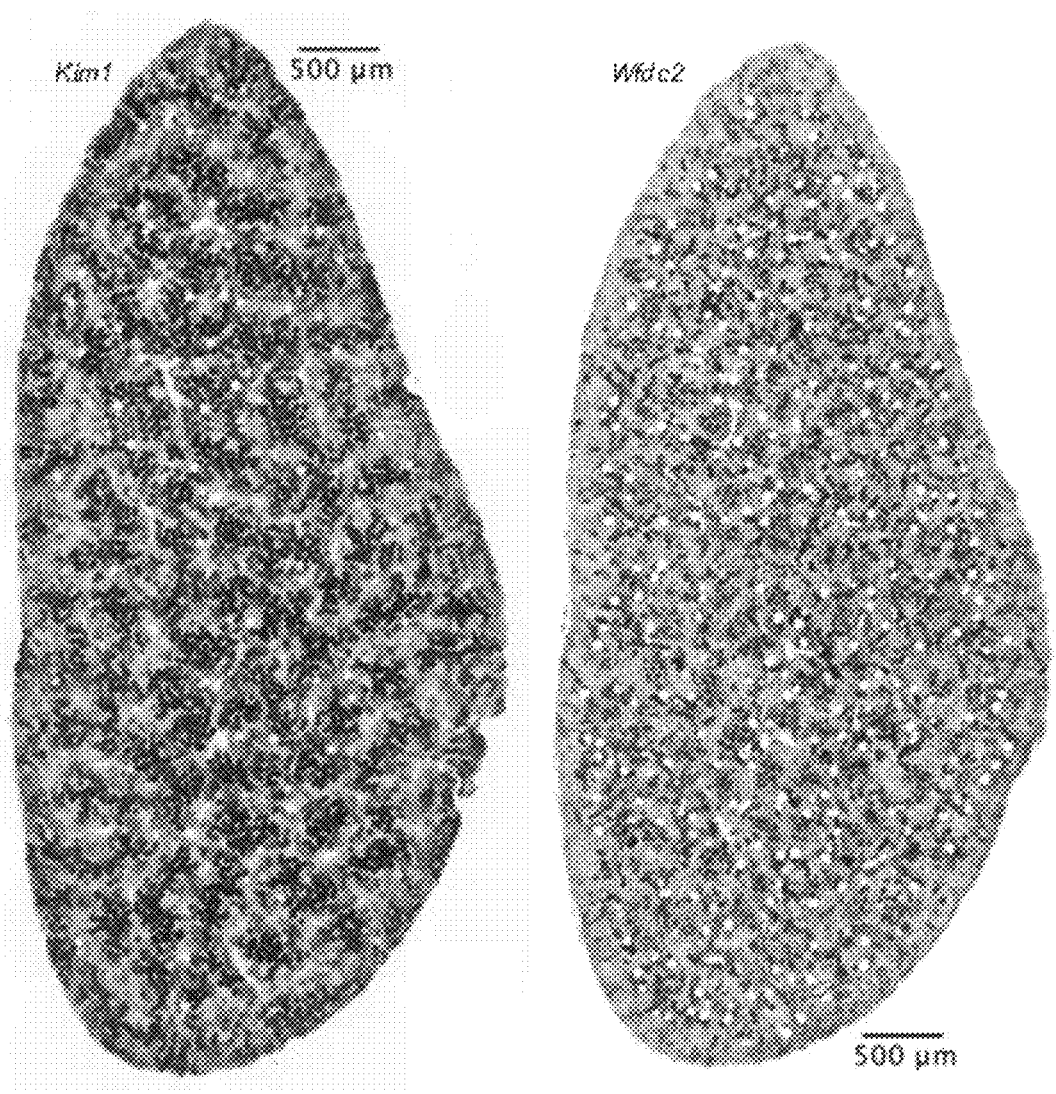
FIG. 7—For mice in FIG. 4B receiving BSA, comparison of Wfdc2 vs. Kim1 by ISH separately on adjacent serial sections. Scale bar=500 µm.

To explore the potential therapeutic application of WFDC2 in AKI, we intravenously injected recombinant WFDC2 protein 12 h after performing the I/R protocol in mice. Strikingly, after injection, a significant decrease of serum creatinine was observed (FIGS. 4C, 7), as well as decreased Kim1 expression (FIG. 4D-E) and diminished KIM-1 in kidney tissue samples (FIG. 4B). Importantly, WFDC2 was used 12 h after the I/R occurred, which mimics the typical clinical problem in humans.

WAP four-disulfide core domain 2 (WFDC2), encoded by WFDC2, is also known as HE4 and WAP5 and was identified from a human epididymis cDNA library, has sequence similarity to proteinase inhibitors [citing: Kirchhoff, C., Habben, I., Ivell, R. & Krull, N. A major human epididymisspecific cDNA encodes a protein with sequence homology to extracellular proteinase inhibitors. *Biol Reprod* 45, 350-357 (1991)], and inhibits several serine, aspartyl and cysteine proteases in vitro [citing: Chhikara. N. et al. *Human epididymis protein-4 (HE-4): a novel cross-class protease inhibitor. PLoS One* 7. e47672. doi:10.1371/journal.pone.0047672 (2012)]. Subsequently, WFDC2 was found to be overexpressed in ovarian carcinomas and was suggested to induce chemoresistance by activating the AKT and ERK pathways [citing: Hellstrom, I. et al. The HE4 (WFDC2) protein is a biomarker for ovarian carcinoma. *Cancer Res* 63, 3695-3700 (2003); Drapkin, R. et al. Human epididymis protein 4 (HE4) is a secreted glycoprotein that is overexpressed by serous and endometrioid ovarian carcinomas. *Cancer Res* 65, 2162-2169, doi:10.1158/0008-5472.CAN-04-3924 (2005); Lee, S. et al. Role of human epididymis protein 4 in chemoresistance and prognosis of epithelial ovarian cancer. *J Obstet Gynaecol Res* 43, 220-227, doi: 10.1111/jog.13181 (2017)].

Wfdc2 was not highly ranked in the list of gene candidates from our 3D culture model, and was similarly not highly ranked among candidate genes from a mouse model of AKI/CKD [citing: Liu, J. et al. Molecular characterization of the transition from acute to chronic kidney injury following ischemia/reperfusion. *JCI Insight* 2, doi:10.1172/jci.insight.94716 (2017)]. WFDC2 only emerged as a candidate due to our finding of the protein in the lumen in our 3D culture model. Our multi-faceted approach shows that Wfdc2 expression is upregulated in in vitro and murine models of AKI, and in AKI in humans, and correlates with functional recovery in patients. WFDC2 is the first validated downstream target of Kim1 that has a therapeutic effect in an AKI mouse model.

A previous study suggested that intact KIM-1 reduces acute injury by increasing phagocytosis, thereby mitigating inflammation [citing: Yang, L. et al. KIM-1-mediated phagocytosis reduces acute injury to the kidney. *J Clin Invest* 125, 1620-1636, doi:10.1172/JCI75417 (2015)]; this is compatible with our results. Our results indicate that Wfdc2 can be upregulated by the extracellular domain of KIM-1 (FIG. 3A-B,E), and can promote recovery by accelerating lumen formation.

The metanephric kidney has one of most complex geometric structures of any organ and we suggest that this may be central to the mechanism of the KIM-1-WFDC2 axis. One possibility is that the extracellular KIM-1 fragment first travels down the nephron from the proximal tubule through the medulla to the distal tubule, where it induces secretion of WFDC2. In turn, WFDC2 acts on the proximal tubule, which in absolute distance is close to the distal tubule. Additionally, the permeability barrier and polarity of the proximal tubule is temporarily abrogated by the AKI damage.

Our findings that administration of WFDC2 after I/R injury in mouse promoted recovery and that WFDC2 expression correlated with clinical outcome raise the possibility that WFDC2 may offer a long-sought, specific therapy for human AKI.

Experimental Procedures

Reagents and Materials

Commercial antibodies were obtained from Abcam (KIM-1, cat #PA5-20244), Jackson ImmunoResearch (Alexa Fluor 647 conjugated secondary antibodies) and ProteinTech (GAPDH, cat #60004-1-Ig). Purified recombinant human WFDC2 protein (cat #12609-H08H), human KIM-1 protein (cat #11051-HNCH) were obtained from Sino Biological. All other materials were from Sigma or Sangon unless otherwise indicated.

Cell Culture, Transient Transfection and Viral Transduction

MDCK cells were cultured in MEM supplemented with 5% FBS (HyClone), 100 U/ml penicillin, 100 µg/ml streptomycin and 1× GlutaMax (Gibco). Transient transfections were performed using Lipofectamine 2000 (Invitrogen) and Opti-MEM (Gibco). Viral packaging, infection and fluorescence-activated cell sorting were as described [citing: Cai, L., Holoweckyj, N., Schaller, M. D. & Bear, J. E. Phosphorylation of coronin 1B by protein kinase C regulates interaction with Arp2/3 and cell motility. J Biol Chem 280, 31913-31923, doi:10.1074/jbc.M504146200 (2005)].

MDCK cysts were grown in Matrigel (Corning). Cells were re-plated 24 h before the experiments. On day 0, MDCK cells were trypsinized to a single cell suspension. 4500 cells in 250 µl 2% Matrigel were plated into one well of 8-well #1.5 coverglass chambers (Nunc), which was pre-coated with 4 µl of 100% Matrigel and solidified at 37° C. for 10 min. Cysts were grown for the indicated time before fixation in 4% paraformaldehyde. To grow mosaic cysts, the indicated types of cells were gently mixed before plating.

Constructs and Molecular Cloning

PCR and subcloning were performed using standard methods. All constructs were verified by Sanger sequencing.

Mouse Ischemic/Reperfusion (I/R) Injury

Experiments were approved by the International Animal Care and Use Committee of Fudan University and adhered strictly to the National Institutes of Health Guide for the Care and Use of Laboratory Animals.

A warm kidney I/R model [citing: Wei, Q. & Dong, Z. Mouse model of ischemic acute kidney injury: technical notes and tricks. Am J Physiol Renal Physiol 303, F1487-1494, doi:10.1152/ajprenal.00352.2012 (2012). Xu, X. et al. Delayed ischemic preconditioning contributes to renal protection by upregulation of miR-21. Kidney Int 82, 1167-1175, doi:10.1038/ki.2012.241 (2012)] was induced in 8-week-old male C57BL/6 mice (20-25 g; Animal Center of Fudan University, Shanghai, China). In brief, anesthesia was induced with intraperitoneal sodium pentobarbital (50 mg/kg body weight) and kidney I/R was induced by bilateral kidney pedicle clamping with micro-aneurysm clips for 35 min, followed by reperfusion for the indicated time. Mice were placed on a heating pan under a warming light to maintain 37° C. core body temperature. Sham controls underwent the identical surgical procedures except vascular occlusion. Recombinant WFDC2 protein (0.2 ml, 25 µg/ml in 0.9% NaCl) was injected into the tail vein of mice 12 h after reperfusion, whereas control animals received BSA (0.2 ml, 25 µg/ml in 0.9% NaCl).

Gene Expression Analysis

For microarray analysis, total RNA of MDCK cells at indicated stages were extracted using Trizol (Invitrogen), and further purified and concentrated with RNeasy MinElute column (Qiagen). RNA labeling, hybridization and scanning of Canine Gene Expression Microarray 4×44K (Agilent), and data extraction were performed in the Sandler UCSF Asthma Basic Research Center Functional Genomics Core Facility. The microarray data is available upon reasonable request.

For real-time PCR analysis, mouse kidneys at 6, 12, 24 or 48 h after I/R were homogenized in Trizol, RNA was extracted, and complementary DNA (cDNA) was reverse-transcribed using a cDNA synthesis kit (Vazyme, catalog #R211-01). Realtime PCR was carried out with the kidney cDNA using EvaGreen PCR Master Mix on a CFX Manager System (Bio-Rad) in triplicate. Measurements were standardized to Gapdh or 18S rRNA, and normalized to sham kidneys. Primer sequences are provided in Suppl. Table 3.

Histology

We analyzed gene expression by ISH [citing: Xu, X. et al. Modular genetic control of sexually dimorphic behaviors. Cell 148, 596-607, doi:10.1016/j.cell.2011.12.018 (2012)] on 30-µm thick serial sections, prepared by a vibratome (Leica, VT1200) that spanned the renal cortex and medulla of mouse kidneys. Probes for ISH were generated from subcloned RT-PCR products, and primer sequences are provided in Suppl. Table 3. Glass slides with kidney sections were hybridized with 0.5 µg/ml of the indicated probe at 65° C. for 10 h, washed and incubated with alkaline phosphatase conjugated sheep anti-digoxigenin antibody (1:2000, Roche, cat #11093274910) at 4° C. on a rocking bed for 10 h. Hybridization was visualized with the histochemical substrates 5-bromo-4-chloro-3-indolylphosphate and nitro blue tetrazolium subsequent to incubation at 37° C. The labeling was imaged using bright field optics with an inverted microscope (IX81, Olympus) and an sCMOS camera (DS-Qi2, Nikon).

Human Kidney Biopsies and ISH

The study was approved by the Clinical Research Ethical Committee of the Zhongshan Hospital, Fudan University. All patients provided informed consent. Clinical data was recorded at the time of admission and hospital discharge [citing: Moore, H. M. et al. Biospecimen reporting for improved study quality (BRISQ). *Cancer Cytopathol* 119, 92-101, doi:10.1002/cncy.20147 (2011)]. Kidney biopsies were fixed in 10% neutral buffered formalin, dehydrated and embedded in paraffin. Paraffin sections were rehydrated and moved into PBS (DEPC-treated) before ISH.

Serum Creatinine Test

Blood samples (1 ml each) were collected from mouse hearts at 24 h after I/R, before extracting the kidneys. Plasma was prepared by centrifugation (5 min, 3300×g, 4° C.), frozen and stored at −20° C. until analysis. Serum creatinine was measured using QuantiChrom™ Creatinine Assay Kit (BioAssay Systems, cat #DICT-500).

Light Microscopy, Image Analysis and Statistical Analysis

Epifluorescent images were captured using an inverted microscope (IX81, Olympus) and an sCMOS camera (Zyla5.5, Andor). Optical sections were captured using a spinning disk confocal scan head (CSU-X/M2N, Yokogawa) attached to an IX81 and an EMCCD camera (DU897BV, Andor). Microscopes were controlled by Micro-Manager software [citing: Edelstein, A., Amodaj, N., Hoover, K., Vale, R. & Stuurman, N. Computer control of microscopes using microManager. *Curr Protoc Mol Biol Chapter* 14, Unit14 20, doi:10.1002/0471142727.mb1420s92 (2010). Edelstein, A. D. et al. Advanced methods of microscope control using muManager software. *J Biol Methods* 1, doi:10.14440/jbm.2014.36 (2014)].

All statistical analysis was performed using Prism (Graphpad) and ImageJ [citing: Cai, L., Makhov, A. M., Schafer, D. A. & Bear, J. E. Coronin 1B antagonizes cortactin and remodels Arp2/3-containing actin branches in lamellipodia. *Cell* 134, 828-842, doi:10.1016/j.cell.2008.06.054 (2008). Schneider, C. A., Rasband, W. S. & Eliceiri, K. W. NIH Image to ImageJ: 25 years of image analysis. *Nat Methods* 9, 671-675 (2012)].

All experiments were independently performed in triplicate and presented as mean±standard deviation; unless otherwise indicated. Images were combined and annotated in Powerpoint (Microsoft) for presentation. Representative images are shown.

| | | Recovered | Not fully recovered[a] |
|---|---|---|---|
| Age (year) | | 31, 36, 41, 63 | 37, 38, 77 |
| Urine (mL/6 hr) | Pre | 2200, 3000, 0, 1200 | 2500, 1300, 1500 |
| | After | 2000, 2500, 2000, 2000 | 2000, 1500, 800 |
| Scr (μM) | Pre | 140, 266, 1201, 872 | 283, 859, 644 |
| | After[b] | 80, 82, 134, 100 | 314, 300, 703 |
| WFDC2+ tubules (%) | | 39.4, 30.9, 30.2, 52.0 | 13.9, 12.2, NA. |

Suppl. Table 1

[a]Fully recovered was estimated as described in Kellum JA. Nephron Clin Pract, 2014;127:81-88 (doi: 10.1159/000363681)
[b]Based on the level of serum creatinine (Scr) on day 28 after diagnosis

SUPPL. TABLE 2

SUMMARY:
Mosaic cysts developed from canine MDCK cells were used in microarray experiments to examine the process of cell death and recovery in the epithelial wall. Parts of the cyst were killed and the remainder was allowed to recover. Two populations of cells were examined (G0/G1 and S/G2/M) at 3 different time points (control, 12 and 24 hours after cell wounding).

GG_12vsGG_C: AdjP < 0.05

| No | ProbeID | Accession | GeneSymbol | Description |
|---|---|---|---|---|
| 1 | A_11_P0000027492 | XM_540284 | LOC483166 | PREDICTED: Canis familiaris similar to germinal histone H4 gene (LOC483166), mRNA [XM_540284] |
| 2 | A_11_P0000019891 | NM_001003173 | LOC403800 | Canis familiaris metallothionein-1 (LOC403800), mRNA [NM_001003173] |
| 3 | A_11_P0000032894 | XM_546853 | LOC48973 3 | PREDICTED: Canis familiaris similar to nin one binding protein (LOC489733), mRNA [XM_546853] |
| 4 | A_11_P0000041800 | TC45204 | TC45204 | AF040105 RCL {Homo sapiens;}, partial (61%) [TC45204] |

SUPPL. TABLE 2-continued

SUMMARY:
Mosaic cysts developed from canine MDCK cells were used in microarray experiments to examine
the process of cell death and recovery in the epithelial wall. Parts of the cyst were
killed and the remainder was allowed to recover. Two populations of cells were examined
(G0/G1 and S/G2/M) at 3 different time points (control, 12 and 24 hours after cell wounding).

| | | | | |
|---|---|---|---|---|
| 5 | A_11_P0000039264 | TC33925 | TC33925 | IF5A_BOVIN (Q6EWQ7) Eukaryotic translation initiation factor 5A (eIF-5A) (eIF-4D), partial (66%) [TC33925] |
| 6 | A_11_P0000006353 | CN005642 | CN005642 | ip33d03.g1 Brain - Cerebellum Library (DOGEST8) Canis familiaris cDNA clone ip33d03, mRNA sequence [CN005642] |
| 7 | A_11_P0000025363 | XM_537648 | LOC480527 | PREDICTED: Canis familiaris similar to CDC6 homolog (LOC480527), mRNA [XM_537648] |
| 8 | A_11_P0000031185 | XM_544736 | LOC487611 | PREDICTED: Canis familiaris similar to likely ortholog of mouse klotho lactase-phlorizin hydrolase related protein (LOC487611), mRNA [XM_544736] |
| 9 | A_11_P0000023855 | XM_535906 | LOC478739 | PREDICTED: Canis familiaris similar to Geminin (LOC478739), mRNA [XM_535906] |
| 10 | A_11_P0000002 2046 | XM_533750 | LOC476544 | PREDICTED: Canis familiaris similar to postreplication repair protein hRAD18p (LOC476544), mRNA [XM_533750] |
| 11 | A_11_P00000780 | ENSCAFT00000025132 | ENSCAFT00000025132 | PSB6_HUMAN (P28072) Proteasome subunit beta type 6 precursor (Proteasome delta chain) (Macropain delta chain) |

SUPPL. TABLE 2-continued

SUMMARY:
Mosaic cysts developed from canine MDCK cells were used in microarray experiments to examine the process of cell death and recovery in the epithelial wall. Parts of the cyst were killed and the remainder was allowed to recover. Two populations of cells were examined (G0/G1 and S/G2/M) at 3 different time points (control, 12 and 24 hours after cell wounding).

| # | | | | |
|---|---|---|---|---|
| | | | | (Multicatalytic endopeptidase complex delta chain) (Proteasome subunit Y), complete [TC40924] |
| 12 | A_11_P0000038976 | TC32626 | TC32626 | UCRY_MOUSE (Q9CPX8) Ubiquinol-cytochrome C reductase complex 6.4 kDa protein (Complex III subunit XI), partial (98%) [TC32626] |
| 13 | A_11_P0000023810 | XM_535852 | LOC478683 | PREDICTED: Canis familiaris LOC478683 (LOC478683), mRNA [XM_535852] |
| 14 | A_11_P0000026028 | XM_538494 | LOC481373 | PREDICTED: Canis familiaris similar to EML5 (LOC481373), mRNA [XM_538494] |
| 15 | A_11_P0000013540 | CO718726 | CO718726 | DG14-6i21 DG14-muscle Canis familiaris cDNA 3', mRNA sequence [CO718726] |
| 16 | A_11_P0000024760 | XM_536947 | LOC479820 | PREDICTED: Canis familiaris similar to Exonuclease NEF-sp (LOC479820), mRNA [XM_536947] |
| 17 | A_11_P0000016579 | DN746739 | DN746739 | GL-Cf-3531 GLGC-LIB0001-cf Canis familiaris Normalized Mixed Tissue cDNA Library Canis familiaris cDNA, mRNA sequence [DN746739] |
| 18 | A_11_P0000014990 | DN372532 | DN372532 | LIB3733-049-A1-K1-E4 LIB3733 Canis familiaris cDNA clone CLN12921657, mRNA sequence [DN372532] |

SUPPL. TABLE 2-continued

SUMMARY:
Mosaic cysts developed from canine MDCK cells were used in microarray experiments to examine the process of cell death and recovery in the epithelial wall. Parts of the cyst were killed and the remainder was allowed to recover. Two populations of cells were examined (G0/G1 and S/G2/M) at 3 different time points (control, 12 and 24 hours after cell wounding).

| | | | | |
|---|---|---|---|---|
| 19 | A_11_P0000015068 | DN376504 | DN376504 | LIB38529_003_B05_T7_1 LIB38529 Canis familiaris cDNA clone LIB38529_003_B05, mRNA sequence [DN376504] |
| 20 | A_11_P0000021810 | XM_533466 | SLC22A2 | PREDICTED: Canis familiaris solute carrier family 22, member 2 (SLC22A2), mRNA [XM_533466] |
| 21 | A_11_P0000020381 | XM_531761 | LOC474532 | PREDICTED: Canis familiaris similar to hypothetical protein MGC40368 (LOC474532), mRNA [XM_531761] |
| 22 | A_11_P0000041847 | TC45410 | TC45410 | BC033803 limbic system-associated membrane protein {Homo sapiens;}, partial (20%) [TC45410] |
| 23 | A_11_P0000021063 | XM_532594 | LOC475370 | PREDICTED: Canis familiaris similar to tetraspan TM4SF; Tspan-1 (LOC475370), mRNA [XM_532594] |
| 24 | A_11_P000005049 | CF411007 | CF411007 | CH3#070_H02MF Canine heart normalized cDNA Library in pBluescript Canis familiaris cDNA clone CH3#070_H02 5', mRNA sequence [CF411007] |
| 25 | A_11_P0000034907 | XM_549343 | LOC492223 | PREDICTED: Canis familiaris similar to gamma-aminobutyric acid A receptor, alpha 3 precursor (LOC492223), mRNA [XM_549343] |

SUPPL. TABLE 2-continued

SUMMARY:
Mosaic cysts developed from canine MDCK cells were used in microarray experiments to examine the process of cell death and recovery in the epithelial wall. Parts of the cyst were killed and the remainder was allowed to recover. Two populations of cells were examined (G0/G1 and S/G2/M) at 3 different time points (control, 12 and 24 hours after cell wounding).

| # | Probe | Accession | Gene | Description |
|---|---|---|---|---|
| 26 | A_11_P0000040455 | TC39136 | TC39136 | Q9Y5L6 (Q9Y5L6) Apoptosis related protein APR-5 (Fragment), partial (9%) [TC39136] |
| 27 | A_11_P0000023755 | XM_535790 | LOC478616 | PREDICTED: Canis familiaris similar to AKAP-associated sperm protein (LOC478616), mRNA [XM_535790] |
| 28 | A_11_P0000030426 | XM_543825 | LOC486698 | PREDICTED: Canis familiaris similar to KIAA1238 protein (LOC486698), mRNA [XM_543825] |
| 29 | A_11_P0000032381 | XM_546250 | SLIT3 | PREDICTED: Canis familiaris similar to slit homolog 3 (LOC489132), mRNA [XM_546250] |
| 30 | A_11_P0000019878 | NM_001003160 | CAN2DD | Canis familiaris dimeric dihydrodiol dehydrogenase (CAN2DD), mRNA [NM_001003160] |
| 31 | A_11_P0000038750 | TC31728 | TC31728 | MIECCOMP Equus caballus mitochondrial DNA complete sequence, partial (4%) [TC31728] |
| 32 | A_11_P0000015149 | DN381350 | DN381350 | LIB38534_052_B02_T7_1 LIB38534 Canis familiaris cDNA clone LIB38534_52_B02, mRNA sequence [DN381350] |
| 33 | A_11_P0000019847 | NM_001003126 | RPGR | Canis familiaris retinitis pigmentosa GTP-ase regulator RPGR (RPGR), mRNA [NM_001003126] |

SUPPL. TABLE 2-continued

SUMMARY:
Mosaic cysts developed from canine MDCK cells were used in microarray experiments to examine the process of cell death and recovery in the epithelial wall. Parts of the cyst were killed and the remainder was allowed to recover. Two populations of cells were examined (G0/G1 and S/G2/M) at 3 different time points (control, 12 and 24 hours after cell wounding).

| | | | | |
|---|---|---|---|---|
| 34 | A_11_P0000011467 | CO682886 | CO682886 | DG11-160f6 DG11-kidney Canis familiaris cDNA 3', mRNA sequence [CO682886] |
| 35 | A_11_P0000012152 | CO692597 | CO692597 | DG11-4o5 DG11-kidney Canis familiaris cDNA 3', mRNA sequence [CO692597] |
| 36 | A_11_P0000012349 | CO695806 | CO695806 | DG11-8k9 DG11-kidney Canis familiaris cDNA 3', mRNA sequence [CO695806] |
| 37 | A_11_P0000012092 | CO691449 | CO691449 | DG11-32c9 DG11-kidney Canis familiaris cDNA 3', mRNA sequence [CO691449] |
| 38 | A_11_P0000013569 | CO719127 | CO719127 | DG14-77o20 DG14-muscle Canis familiaris cDNA 3', mRNA sequence [CO719127] |

GG_12vsGG_C: AdjP < 0.05

| No | Genomic Coordinates | ShortName | GG_12.aveA | GG_C.aveA |
|---|---|---|---|---|
| 1 | chr17: 61819524-61819583 | LOC483166 | 13.022 | 10.937 |
| 2 | chr2: 60240600-60240541 | LOC403800 | 12.502 | 10.486 |
| 3 | chr5: 83075200-83075259 | LOC489733 | 10.334 | 8.637 |
| 4 | chr12: 14643464-14643405 | TC45204 | 10.889 | 9.332 |
| 5 | chr5: 35244398-35244457 | TC33925 | 11.335 | 9.854 |
| 6 | chr6: 040633700-040633759 | CN005642 | 12.42 | 10.975 |
| 7 | chr9: 14976753-14976694 | LOC480527 | 7.165 | 5.721 |
| 8 | chr30: 33753441-33751930 | LOC487611 | 7.361 | 6.016 |
| 9 | chr35: 25780447-25780506 | LOC478739 | 10.037 | 8.782 |

SUPPL. TABLE 2-continued

SUMMARY:
Mosaic cysts developed from canine MDCK cells were used in microarray experiments to examine
the process of cell death and recovery in the epithelial wall. Parts of the cyst were
killed and the remainder was allowed to recover. Two populations of cells were examined
(G0/G1 and S/G2/M) at 3 different time points (control, 12 and 24 hours after cell wounding).

| | | | | |
|---|---|---|---|---|
| 10 | chr20: 12110783-12110842 | LOC476544 | 9.057 | 8.064 |
| 11 | chr5: 34747895-34747836 | ENSCAFT00000025132 | 12.682 | 11.693 |
| 12 | chr20: 60309088-60309029 | TC32626 | 13.331 | 12.361 |
| 13 | chr34: 35340187-35333162 | LOC478683 | 5.232 | 6.188 |
| 14 | chr10: 59259242-59259301 | LOC481373 | 5.55 | 6.573 |
| 15 | | CO718726 | 8.857 | 9.948 |
| 16 | chr6: 26151795-26150394 | LOC479820 | 5.895 | 7.053 |
| 17 | | DN746739 | 8.18 | 9.347 |
| 18 | chr6: 34993617-34993558 | DN372532 | 6.802 | 8.146 |
| 19 | chr16: 14995357-14995416 | DN376504 | 7.696 | 9.063 |
| 20 | | SLC22A2 | 8.476 | 9.876 |
| 21 | chr10: 35585025-35583726 | LOC474532 | 5.001 | 6.469 |
| 22 | chr33: 22909627-22909567 | TC45410 | 7.411 | 8.919 |
| 23 | chr15: 17170783-17170724 | LOC475370 | 10.396 | 11.953 |
| 24 | chr22: 51481040-51481099 | CF411007 | 7.735 | 9.301 |
| 25 | chrX: 123182076-123182017 | LOC492223 | 10.484 | 12.065 |
| 26 | chr15: 21107956-21107897 | TC39136 | 4.699 | 6.302 |
| 27 | chr34: 6795793-6795734 | LOC478616 | 5.58 | 7.185 |
| 28 | chr27: 39917800-39917741 | LOC486698 | 8.664 | 10.278 |
| 29 | chr4: 46242856-46242915 | SLIT3 | 7.21 | 8.859 |
| 30 | | CAN2DD | 6.833 | 8.492 |
| 31 | chrM: 5798-5857 | TC31728 | 7.108 | 8.782 |
| 32 | chr38: 4808440-4808381 | DN381350 | 6.039 | 7.92 |
| 33 | chrX: 32896873-32896814 | RPGR | 5.49 | 7.419 |
| 34 | chr22: 51487724-51487662 | CO682886 | 7.008 | 9.046 |
| 35 | chr7: 021236162-021236103 | CO692597 | 6.677 | 8.759 |
| 36 | chr3: 74183674-74183615 | CO695806 | 7.857 | 10.068 |

SUPPL. TABLE 2-continued

SUMMARY:
Mosaic cysts developed from canine MDCK cells were used in microarray experiments to examine the process of cell death and recovery in the epithelial wall. Parts of the cyst were killed and the remainder was allowed to recover. Two populations of cells were examined (G0/G1 and S/G2/M) at 3 different time points (control, 12 and 24 hours after cell wounding).

| | | | | | |
|---|---|---|---|---|---|
| 37 | chr24: 35699393-35699335 | CO691449 | | 8.73 | 10.968 |
| 38 | chr4: 46261653-46261595 | CO719127 | | 5.802 | 8.05 |

GG_12vsGG_C

| No | M | Fold | AdjP | FDR | B |
|---|---|---|---|---|---|
| 1 | 2.084 | 4.241 | 0.04332 | 0.00121 | 5.332 |
| 2 | 2.016 | 4.045 | 0.00345 | 0.00031 | 7.647 |
| 3 | 1.697 | 3.242 | 0.01809 | 0.00091 | 6.141 |
| 4 | 1.557 | 2.942 | 7e−05 | 2e−05 | 10.995 |
| 5 | 1.481 | 2.792 | 0.005 | 0.00042 | 7.314 |
| 6 | 1.445 | 2.723 | 0.03478 | 0.0012 | 5.536 |
| 7 | 1.444 | 2.72 | 0.03074 | 0.00114 | 5.651 |
| 8 | 1.346 | 2.541 | 0.0489 | 0.00129 | 5.219 |
| 9 | 1.255 | 2.386 | 0.01625 | 0.00086 | 6.239 |
| 10 | 0.992 | 1.989 | 0.03608 | 0.0012 | 5.502 |
| 11 | 0.989 | 1.985 | 0.01527 | 0.00085 | 6.296 |
| 12 | 0.97 | 1.959 | 0.034 | 0.0012 | 5.557 |
| 13 | 0.956 | 0.515 | 0.03922 | 0.00121 | 5.425 |
| 14 | 1.023 | 0.492 | 0.01378 | 0.00085 | 6.39 |
| 15 | 1.091 | 0.469 | 0.01462 | 0.00085 | 6.336 |
| 16 | 1.158 | 0.448 | 0.04174 | 0.00121 | 5.367 |
| 17 | 1.167 | 0.445 | 0.04613 | 0.00125 | 5.274 |
| 18 | 1.344 | 0.394 | 0.02398 | 0.00096 | 5.88 |
| 19 | 1.367 | 0.388 | 0.02029 | 0.00092 | 6.035 |
| 20 | −1.4 | 0.379 | 0.01129 | 0.00079 | 6.573 |
| 21 | 1.468 | 0.361 | 6e−05 | 2e−05 | 11.132 |
| 22 | 1.508 | 0.352 | 0.02815 | 0.00108 | 5.732 |
| 23 | 1.557 | 0.34 | 0.00259 | 0.00029 | 7.902 |
| 24 | 1.565 | 0.338 | 0.04196 | 0.00121 | 5.362 |
| 25 | 1.581 | 0.334 | 0.00211 | 0.00026 | 8.087 |
| 26 | 1.602 | 0.329 | 0.04342 | 0.00121 | 5.33 |
| 27 | 1.604 | 0.329 | 4e−05 | 2e−05 | 11.439 |
| 28 | 1.613 | 0.327 | 0.02131 | 0.00092 | 5.99 |
| 29 | 1.648 | 0.319 | 0.00287 | 0.00029 | 7.81 |
| 30 | 1.659 | 0.317 | 0.00043 | 9e−05 | 9.473 |
| 31 | 1.675 | 0.313 | 0.00811 | 0.00062 | 6.875 |
| 32 | 1.881 | 0.272 | 0.02203 | 0.00092 | 5.959 |
| 33 | 1.929 | 0.263 | 6e−04 | 9e−05 | 9.185 |
| 34 | 2.038 | 0.244 | 0.00057 | 9e−05 | 9.235 |
| 35 | 2.082 | 0.236 | 0.03787 | 0.00121 | 5.457 |
| 36 | 2.211 | 0.216 | 0.02057 | 0.00092 | 6.022 |
| 37 | 2.237 | 0.212 | 0.01186 | 0.00079 | 6.528 |
| 38 | 2.248 | 0.21 | 0.00013 | 3e−05 | 10.508 |

GG_24vsGG_C: AdjP < 0.05

| No | ProbeID | Accession | GeneSymbol | Description |
|---|---|---|---|---|
| 1 | A_11_P0000032894 | XM_546853 | LOC489733 | PREDICTED: Canis familiaris similar to nin one binding protein (LOC489733), mRNA [XM_546853] |
| 2 | A_11_P0000016788 | DN748198 | DN748198 | GL-Cf-4990 GLGC-LIB0001-cf Canis familiaris Normalized Mixed Tissue cDNA Library Canis familiaris cDNA, mRNA sequence [DN748198] |
| 3 | A_11_P0000022895 | XM_534758 | LOC477563 | PREDICTED: Canis familiaris similar to Ran-specific GTPase-activating protein (Ran binding protein 1) |

SUPPL. TABLE 2-continued

SUMMARY:
Mosaic cysts developed from canine MDCK cells were used in microarray experiments to examine the process of cell death and recovery in the epithelial wall. Parts of the cyst were killed and the remainder was allowed to recover. Two populations of cells were examined (G0/G1 and S/G2/M) at 3 different time points (control, 12 and 24 hours after cell wounding).

| | | | | |
|---|---|---|---|---|
| | | | | (RANBP1) (HpaII tiny fragments locus 9a protein) (LOC477563), mRNA [XM_534758] |
| 4 | A_11_P0000034047 | XM_548200 | LOC491080 | PREDICTED: Canis familiaris similar to hypothetical protein PRO1855 (LOC491080), mRNA [XM_548200] |
| 5 | A_11_P0000027576 | XM_540388 | LOC483269 | PREDICTED: Canis familiaris similar to Hypothetical pseudouridine synthase KIAA1897 (LOC483269), mRNA [XM_540388] |
| 6 | A_11_P0000041800 | TC45204 | TC45204 | AF040105 RCL {Homo sapiens;}, partial (61%) [TC45204] |
| 7 | A_11_P0000023151 | XM_535063 | LOC477871 | PREDICTED: Canis familiaris similar to Minichromosome maintenance protein 4 (LOC477871), mRNA [XM_535063] |
| 8 | A_11_P0000021349 | XM_532927 | LOC475719 | PREDICTED: Canis familiaris LOC475719 (LOC475719), mRNA [XM_532927] |
| 9 | A_11_P0000024479 | XM_536633 | LOC479494 | PREDICTED: Canis familiaris similar to RAN guanine nucleotide release factor (LOC479494), mRNA [XM_536633] |
| 10 | A_11_P0000020337 | XM_531713 | LOC474484 | PREDICTED: Canis familiaris similar to NHP2-like protein 1 (High mobility group-like nuclear protein 2 homolog 1) ([U4/U6.U5] tri-snRNP 15.5 kDa protein) (Sperm specific antigen 1) (Fertilization antigen 1) (FA-1) (LOC474484), mRNA [XM_531713] |
| 11 | A_11_P0000021627 | XM_533244 | LOC476035 | PREDICTED: Canis familiaris similar to protein phosphatase 1, regulatory (inhibitor) subunit 14B (LOC476035), mRNA [XM_533244] |
| 12 | A_11_P0000022821 | XM_534673 | LOC477475 | PREDICTED: Canis familiaris similar to hypothetical protein (LOC477475), mRNA [XM_534673] |
| 13 | A_11_P0000020975 | XM_532493 | LOC475258 | PREDICTED: Canis familiaris similar to cytochrome c - dog (tentative sequence) (LOC475258), mRNA [XM_532493] |

SUPPL. TABLE 2-continued

SUMMARY:
Mosaic cysts developed from canine MDCK cells were used in microarray experiments to examine the process of cell death and recovery in the epithelial wall. Parts of the cyst were killed and the remainder was allowed to recover. Two populations of cells were examined (G0/G1 and S/G2/M) at 3 different time points (control, 12 and 24 hours after cell wounding).

| | | | | |
|---|---|---|---|---|
| 14 | A_11_P0000024712 | XM_536894 | LOC479766 | PREDICTED: Canis familiaris similar to Eukaryotic translation initiation factor 3 subunit 9 (eIF-3 eta) (eIF3 p116) (eIF3 p110) (eIF3b) (LOC479766), mRNA [XM_536894] |
| 15 | A_11_P0000020959 | XM_532473 | LOC475240 | PREDICTED: Canis familiaris similar to asparagine synthetase (LOC475240), mRNA [XM_532473] |
| 16 | A_11_P0000039264 | TC33925 | TC33925 | IF5A_BOVIN (Q6EWQ7) Eukaryotic translation initiation factor 5A (eIF-5A) (eIF-4D), partial (66%) [TC33925] |
| 17 | A_11_P0000019826 | NM_001003105 | TUBG | Canis familiaris gamma tubulin (TUBG), mRNA [NM_001003105] |
| 18 | A_11_P0000017013 | DN751741 | DN751741 | GL-Cf-8534 GLGC-LIB0001-cf Canis familiaris Normalized Mixed Tissue cDNA Library Canis familiaris cDNA, mRNA sequence [DN751741] |
| 19 | A_11_P0000021743 | XM_533382 | LOC476177 | PREDICTED: Canis familiaris LOC476177 (LOC476177), mRNA [XM_533382] |
| 20 | A_11_P0000025982 | XM_538439 | LOC481318 | PREDICTED: Canis familiaris similar to UDP-glucuronic acid decarboxylase (LOC481318), mRNA [XM_538439] |
| 21 | A_11_P0000023855 | XM_535906 | LOC478739 | PREDICTED: Canis familiaris similar to Geminin (LOC478739), mRNA [XM_535906] |
| 22 | A_11_P00000824 | ENSCAFT00000026424 | ENSCAFT00000026424 | Q5Z8N8 (Q5Z8N8) Aspartic proteinase nepenthesin II-like, partial (6%) [TC32227] |
| 23 | A_11_P0000039653 | TC35778 | TC35778 | A32348 alpha-antigen B precursor, extracellular - Mycobacterium bovis {Mycobacterium bovis;}, partial (6%) [TC35778] |
| 24 | A_11_P0000024270 | XM_536387 | LOC479245 | PREDICTED: Canis familiaris similar to tetratricopeptide repeat domain 18 (LOC479245), mRNA [XM_536387] |
| 25 | A_11_P0000030745 | XM_544209 | LOC487081 | PREDICTED: Canis familiaris similar to BMP and activin membrane-bound inhibitor homolog precursor (Putative transmembrane protein NMA) (Non-metastatic gene A protein) (LOC487081), mRNA [XM_544209] |

SUPPL. TABLE 2-continued

SUMMARY:
Mosaic cysts developed from canine MDCK cells were used in microarray experiments to examine the process of cell death and recovery in the epithelial wall. Parts of the cyst were killed and the remainder was allowed to recover. Two populations of cells were examined (G0/G1 and S/G2/M) at 3 different time points (control, 12 and 24 hours after cell wounding).

| | | | | |
|---|---|---|---|---|
| 26 | A_11_P0000018843 | DN877221 | DN877221 | nae12b06.y1 Dog eye eye minus lens and cornea. Unnormalized (nae) Canis familiaris cDNA clone nae12b06 5', mRNA sequence [DN877221] |
| 27 | A_11_P00000780 | ENSCAFT00000025132 | ENSCAFT00000025132 | PSB6_HUMAN (P28072) Proteasome subunit beta type 6 precursor (Proteasome delta chain) (Macropain delta chain) (Multicatalytic endopeptidase complex delta chain) (Proteasome subunit Y), complete [TC40924] |
| 28 | A_11_P0000013540 | CO718726 | CO718726 | DG14-6i21 DG14-muscle Canis familiaris cDNA 3', mRNA sequence [CO718726] |
| 29 | A_11_P0000011543 | CO683620 | CO683620 | DG11-172c1 DG11-kidney Canis familiaris cDNA 3', mRNA sequence [CO683620] |
| 30 | A_11_P0000029478 | XM_542714 | LOC485595 | PREDICTED: Canis familiaris similar to TPR domain containing STI2 (LOC485595), mRNA [XM_542714] |
| 31 | A_11_P0000023147 | XM_535058 | LOC477866 | PREDICTED: Canis familiaris similar to fibronectin type 3 and ankyrin repeat domains 1 (LOC477866), mRNA [XM_535058] |
| 32 | A_11_P0000028705 | XM_541745 | LOC484631 | PREDICTED: Canis familiaris similar to brefeldin resistant Arf-GEF 2b isoform (LOC484631), mRNA [XM_541745] |
| 33 | A_11_P0000014490 | DN270582 | DN270582 | LIB30321_028_G01_SP6_1 LIB30321 Canis familiaris cDNA clone LIB30321_028_G01, mRNA sequence [DN270582] |
| 34 | A_11_P0000026535 | XM_539101 | LOC481980 | PREDICTED: Canis familiaris similar to odd-skipped-related 2A protein (LOC481980), mRNA [XM_539101] |
| 35 | A_11_P000007868 | CO599122 | CO599122 | DG8-177a24 DG8-testis Canis familiaris cDNA 3', mRNA sequence [CO599122] |
| 36 | A_11_P0000041784 | TC45157 | TC45157 | Q9TV68 (Q9TV68) Dimeric dihydrodiol dehydrogenase, partial (36%) [TC45157] |
| 37 | A_11_P0000039092 | TC33171 | TC33171 | O89816 (O89816) Envelope glycoprotein, partial (10%) [TC33171] |
| 38 | A_11_P000006553 | CO585946 | CO585946 | DG2-122p11 DG2-brain Canis familiaris cDNA 3', mRNA sequence [CO585946] |

SUPPL. TABLE 2-continued

SUMMARY:
Mosaic cysts developed from canine MDCK cells were used in microarray experiments to examine the process of cell death and recovery in the epithelial wall. Parts of the cyst were killed and the remainder was allowed to recover. Two populations of cells were examined (G0/G1 and S/G2/M) at 3 different time points (control, 12 and 24 hours after cell wounding).

| | | | | |
|---|---|---|---|---|
| 39 | A_11_P0000036266 | BM538435 | BM538435 | |
| 40 | A_11_P0000016579 | DN746739 | DN746739 | GL-Cf-3531 GLGC-LIB0001-cf Canis familiaris Normalized Mixed Tissue cDNA Library Canis familiaris cDNA, mRNA sequence [DN746739] |
| 41 | A_11_P0000024760 | XM_536947 | LOC479820 | PREDICTED: Canis familiaris similar to Exonuclease NEF-sp (LOC479820), mRNA [XM_536947] |
| 42 | A_11___P000002899 | BU746162 | BU746162 | CH3#002_C10T7 Canine heart normalized cDNA Library in pBluescript Canis familiaris cDNA clone CH3#002_C10 5', mRNA sequence [BU746162] |
| 43 | A_11___P0000026028 | XM_538494 | LOC481373 | PREDICTED: Canis familiaris similar to EML5 (LOC481373), mRNA [XM_538494] |
| 44 | A_11_P0000011815 | CO687246 | CO687246 | DG11-229k12 DG11-kidney Canis familiaris cDNA 3', mRNA sequence [CO687246] |
| 45 | A_11_P0000022524 | XM_534327 | LOC477136 | PREDICTED: Canis familiaris similar to Protein C20orf26 (LOC477136), mRNA [XM_534327] |
| 46 | A_11_P0000041 | ENSCAFT00000001196 | ENSCAFT0000001196 | dbj Parkin {Homo sapiens}, partial (27%) [BM538799] |
| 47 | A_11_P0000025415 | XM_537707 | LOC480587 | PREDICTED: Canis familiaris similar to breast carcinoma amplified sequence 3 (LOC480587), mRNA [XM_537707] |
| 48 | A_11_P0000032381 | XM_546250 | SLIT3 | PREDICTED: Canis familiaris similar to slit homolog 3 (LOC489132), mRNA [XM_546250] |
| 49 | A_11_P0000025387 | XM_537673 | LOC480551 | PREDICTED: Canis familiaris similar to hypothetical protein FLJ20920 (LOC480551), mRNA [XM_537673] |
| 50 | A_11_P0000027453 | XM_540237 | LOC483121 | PREDICTED: Canis familiaris LOC483121 (LOC483121), mRNA [XM_540237] |
| 51 | A_11___P000006966 | CO590810 | CO590810 | DG2-41p20 DG2-brain Canis familiaris cDNA 3', mRNA sequence [CO590810] |
| 52 | A_11_P0000016384 | DN745414 | DN745414 | GL-Cf-2206 GLGC-LIB0001-cf Canis familiaris Normalized Mixed Tissue cDNA Library Canis familiaris cDNA, mRNA sequence [DN745414] |

SUPPL. TABLE 2-continued

SUMMARY:
Mosaic cysts developed from canine MDCK cells were used in microarray experiments to examine the process of cell death and recovery in the epithelial wall. Parts of the cyst were killed and the remainder was allowed to recover. Two populations of cells were examined (G0/G1 and S/G2/M) at 3 different time points (control, 12 and 24 hours after cell wounding).

| | | | | |
|---|---|---|---|---|
| 53 | A_11_P0000016214 | DN744243 | DN744243 | GL-Cf-1035 GLGC-LIB0001-cf Canis familiaris Normalized Mixed Tissue cDNA Library Canis familiaris cDNA, mRNA sequence [DN744243] |
| 54 | A_11___P000007026 | CO591347 | CO591347 | DG2-48f3 DG2-brain Canis familiaris cDNA 3', mRNA sequence [CO591347] |
| 55 | A_11_P0000038902 | TC32323 | TC32323 | Q632E5 (Q632E5) Biotin synthesis BioY protein, partial (7%) [TC32323] |
| 56 | A_11_P0000013548 | CO718860 | CO718860 | DG14-71j9 DG14-muscle Canis familiaris cDNA 3', mRNA sequence [CO718860] |
| 57 | A_11_P0000041847 | TC45410 | TC45410 | BC033803 limbic system-associated membrane protein {Homo sapiens;}, partial (20%) [TC45410] |
| 58 | A_11_P0000036218 | BM538045 | BM538045 | A SThM {Homo sapiens}, partial (28%) [BM538045] |
| 59 | A_11_P0000035026 | XM_549470 | LOC475915 | PREDICTED: Canis familiaris LOC475915 (LOC475915), mRNA [XM_549470] |
| 60 | A_11_P0000019804 | NM_001003081 | MRP2 | Canis familiaris multidrug resistance protein 2 (MRP2), mRNA [NM_001003081] |
| 61 | A_11_P0000012636 | CO701152 | CO701152 | DG32-195l2 DG32-liver Canis familiaris cDNA 3', mRNA sequence [CO701152] |
| 62 | A_11_P0000013569 | CO719127 | CO719127 | DG14-77o20 DG14-muscle Canis familiaris cDNA 3', mRNA sequence [CO719127] |
| 63 | A_11_P0000023755 | XM_535790 | LOC478616 | PREDICTED: Canis familiaris similar to AKAP-associated sperm protein (LOC478616), mRNA [XM_535790] |
| 64 | A_11_P0000016824 | DN748424 | DN748424 | GL-Cf-5216 GLGC-LIB0001-cf Canis familiaris Normalized Mixed Tissue cDNA Library Canis familiaris cDNA, mRNA sequence [DN748424] |
| 65 | A_11_P0000013599 | CO719536 | CO719536 | DG14-87k5 DG14-muscle Canis familiaris cDNA 3', mRNA sequence [CO719536] |
| 66 | A_11_P0000020381 | XM_531761 | LOC474532 | PREDICTED: Canis familiaris similar to hypothetical protein MGC40368 (LOC474532), mRNA [XM_531761] |

SUPPL. TABLE 2-continued

SUMMARY:
Mosaic cysts developed from canine MDCK cells were used in microarray experiments to examine the process of cell death and recovery in the epithelial wall. Parts of the cyst were killed and the remainder was allowed to recover. Two populations of cells were examined (G0/G1 and S/G2/M) at 3 different time points (control, 12 and 24 hours after cell wounding).

| | | | | |
|---|---|---|---|---|
| 67 | A_11_P0000024753 | XM_536940 | LOC479813 | PREDICTED: Canis familiaris similar to hypothetical protein E030013G06 (LOC479813), mRNA [XM_536940] |
| 68 | A_11_P0000040455 | TC39136 | TC39136 | Q9Y5L6 (Q9Y5L6) Apoptosis related protein APR-5 (Fragment), partial (9%) [TC39136] |
| 69 | A_11_P0000028220 | XM_541186 | LOC484069 | PREDICTED: Canis familiaris LOC484069 (LOC484069), mRNA [XM_541186] |
| 70 | A_11_P0000040207 | TC38144 | TC38144 | Q6P2R5 (Q6P2R5) Pleckstrin homology domain containing, family M (With RUN domain) member 1, partial (8%) [TC38144] |
| 71 | A_11_P0000021497 | XM_533095 | LOC475887 | PREDICTED: Canis familiaris similar to cAMP-dependent protein kinase type II-beta regulatory subunit (LOC475887), mRNA [XM_533095] |
| 72 | A_11_P0000028820 | XM_541886 | LOC484770 | PREDICTED: Canis familiaris similar to glycine cleavage system T-protein (LOC484770), mRNA [XM_541886] |
| 73 | A_11_P0000019878 | NM_001003160 | CAN2DD | Canis familiaris dimeric dihydrodiol dehydrogenase (CAN2DD), mRNA [NM_001003160] |
| 74 | A_11_P0000021063 | XM_532594 | LOC475370 | PREDICTED: Canis familiaris similar to tetraspan TM4SF; Tspan-1 (LOC475370), mRNA [XM_532594] |
| 75 | A_11_P0000024956 | XM_537165 | LOC480043 | PREDICTED: Canis familiaris similar to mKIAA0850 protein (LOC480043), mRNA [XM_537165] |
| 76 | A_11_P0000014990 | DN372532 | DN372532 | LIB3733-049-A1-K1-E4 LIB3733 Canis familiaris cDNA clone CLN12921657, mRNA sequence [DN372532] |
| 77 | A_11_P0000038750 | TC31728 | TC31728 | MIECCOMP Equus caballus mitochondrial DNA complete sequence, partial (4%) [TC31728] |
| 78 | A_11_P0000033795 | XM_547906 | LOC490784 | PREDICTED: Canis familiaris similar to latent transforming growth factor beta binding protein 2 (LOC490784), mRNA [XM_547906] |

SUPPL. TABLE 2-continued

SUMMARY:
Mosaic cysts developed from canine MDCK cells were used in microarray experiments to examine the process of cell death and recovery in the epithelial wall. Parts of the cyst were killed and the remainder was allowed to recover. Two populations of cells were examined (G0/G1 and S/G2/M) at 3 different time points (control, 12 and 24 hours after cell wounding).

| | | | | |
|---|---|---|---|---|
| 79 | A_11_P000005049 | CF411007 | CF411007 | CH3#070_H02MF Canine heart normalized cDNA Library in pBluescript Canis familiaris cDNA clone CH3#070_H02 5', mRNA sequence [CF411007] |
| 80 | A_11_P0000016170 | DN445054 | DN445054 | LIB5338-013-A1-K1-B6 LIB5338 Canis familiaris cDNA clone CLN14233089, mRNA sequence [DN445054] |
| 81 | A_11_P0000034907 | XM_549343 | LOC492223 | PREDICTED: Canis familiaris similar to gamma-aminobutyric acid A receptor, alpha 3 precursor (LOC492223), mRNA [XM_549343] |
| 82 | A_11_P00000570 | ENSCAFT00000018224 | ENSCAFT00000018224 | LIB3934-046-A1-K1-E6 LIB3934 Canis familiaris cDNA clone CLN12936155, mRNA sequence [DN3 94451] |
| 83 | A_11_P0000015149 | DN381350 | DN381350 | LIB38534_052_B02_T7_1 LIB38534 Canis familiaris cDNA clone LIB38534_52_B02, mRNA sequence [DN381350] |
| 84 | A_11_P0000025991 | XM_538449 | LOC481328 | PREDICTED: Canis familiaris similar to interleukin-1 receptor type I (LOC481328), mRNA [XM_538449] |
| 85 | A_11_P0000030426 | XM_543825 | LOC486698 | PREDICTED: Canis familiaris similar to KIAA1238 protein (LOC486698), mRNA [XM_543825] |
| 86 | A_11_P0000032369 | XM_546235 | LOC489117 | PREDICTED: Canis familiaris similar to Dual specificity protein phosphatase 1 (MAP kinase phosphatase-1) (MKP-1) (Protein-tyrosine phosphatase CL100) (Dual specificity protein phosphatase hVH1) (LOC489117), mRNA [XM_546235] |
| 87 | A_11_P0000019847 | NM_001003126 | RPGR | Canis familiaris retinitis pigmentosa GTP-ase regulator RPGR (RPGR), mRNA [NM_001003126 |
| 88 | A_11_P0000032293 | XM_546151 | LOC489033 | PREDICTED: Canis familiaris similar to 6-pyruvoyl-tetrahydropterin synthase/dimerization cofactor of hepatocyte nuclear factor 1 alpha (TCF1) (LOC489033), mRNA [XM_546151] |
| 89 | A_11_P0000028194 | XM_541154 | LOC484037 | PREDICTED: Canis familiaris LOC484037 (LOC484037), mRNA [XM_541154] |
| 90 | A_11_P0000011467 | CO682886 | CO682886 | DG11-160f6 DG11-kidney Canis familiaris cDNA 3', mRNA sequence [CO682886] |

SUPPL. TABLE 2-continued

SUMMARY:
Mosaic cysts developed from canine MDCK cells were used in microarray experiments to examine the process of cell death and recovery in the epithelial wall. Parts of the cyst were killed and the remainder was allowed to recover. Two populations of cells were examined (G0/G1 and S/G2/M) at 3 different time points (control, 12 and 24 hours after cell wounding).

| | | | | |
|---|---|---|---|---|
| 91 | A_11_P0000016601 | DN746939 | DN746939 | GL-Cf-3731 GLGC-LIB0001-cf Canis familiaris Normalized Mixed Tissue cDNA Library Canis familiaris cDNA, mRNA sequence [DN746939] |
| 92 | A_11_P0000012349 | CO695806 | CO695806 | DG11-8k9 DG11-kidney Canis familiaris cDNA 3', mRNA sequence [CO695806] |
| 93 | A_11_P0000012229 | CO693697 | CO693697 | DG11-66124 DG11-kidney Canis familiaris cDNA 3', mRNA sequence [CO693697] |
| 94 | A_11_P0000016484 | DN746102 | DN746102 | GL-Cf-2894 GLGC-LIB0001-cf Canis familiaris Normalized Mixed Tissue cDNA Library Canis familiaris cDNA, mRNA sequence [DN746102] |
| 95 | A_11_P0000024246 | XM_536361 | LOC479219 | PREDICTED: Canis familiaris similar to Early growth response protein 2 (EGR-2) (Krox-20 protein) (AT591) (LOC479219), mRNA [XM_536361] |
| 96 | A_11_P0000028406 | XM_541416 | LOC484300 | PREDICTED: Canis familiaris similar to hypothetical protein (LOC484300), mRNA [XM_541416] |
| 97 | A_11_P0000020078 | NM_001003372 | VNN1 | Canis familiaris TIFF66 (VNN1), mRNA [NM_001003372] |
| 98 | A_11_P0000012092 | CO691449 | CO691449 | DG11-32c9 DG11-kidney Canis familiaris cDNA 3', mRNA sequence [CO691449] |
| 99 | A_11_P0000012152 | CO692597 | CO692597 | DG11-4o5 DG11-kidney Canis familiaris cDNA 3', mRNA sequence [CO692597] |
| 100 | A_11_P0000038748 | TC31721 | TC31721 | CRAB_BOVIN (P02510) Alpha crystallin B chain (Alpha(B)-crystallin), partial (38%) [TC31721] |

GG_24vsGG_C: AdjP < 0.05

| No | Genomic Coordinates | ShortName | GG_24.aveA | GG_C.aveA |
|---|---|---|---|---|
| 1 | chr5: 83075200-83075259 | LOC489733 | 11.155 | 8.637 |
| 2 | chr23: 47202221-47202162 | DN748198 | 10.096 | 8.027 |
| 3 | chr26: 31235873-31233917 | LOC477563 | 9.084 | 7.197 |
| 4 | chr9: 19021893-19017690 | LOC491080 | 10.779 | 8.974 |
| 5 | chr18: 17800849-17800908 | LOC483269 | 9.266 | 7.512 |
| 6 | chr12: 14643464-14643405 | TC45204 | 11.076 | 9.332 |

SUPPL. TABLE 2-continued

SUMMARY:
Mosaic cysts developed from canine MDCK cells were used in microarray experiments to examine
the process of cell death and recovery in the epithelial wall. Parts of the cyst were
killed and the remainder was allowed to recover. Two populations of cells were examined
(G0/G1 and S/G2/M) at 3 different time points (control, 12 and 24 hours after cell wounding).

| | | | | |
|---|---|---|---|---|
| 7 | chr29: 3265874-3265933 | LOC477871 | 9.087 | 7.354 |
| 8 | chr17: 28880244-28880303 | LOC475719 | 10.852 | 9.126 |
| 9 | chr5: 36055052-36055111 | LOC479494 | 10.186 | 8.493 |
| 10 | chr10: 26792216-26792275 | LOC474484 | 11.629 | 9.998 |
| 11 | chr18: 63174238-63174297 | LOC476035 | 12.294 | 10.689 |
| 12 | chr26: 11458607-11458548 | LOC477475 | 10.491 | 8.889 |
| 13 | chr14: 41140121-41140062 | LOC475258 | 10.33 | 8.759 |
| 14 | chr6: 17534089-17534030 | LOC479766 | 12.443 | 10.939 |
| 15 | chr14: 25266844-25266785 | LOC475240 | 11.497 | 10.015 |
| 16 | chr5: 35244398-35244457 | TC33925 | 11.307 | 9.854 |
| 17 | chr9: 13015989-13015930 | TUBG | 9.179 | 7.728 |
| 18 | chr5: 85258392-85258333 | DN751741 | 10.39 | 9.007 |
| 19 | | LOC476177 | 7.868 | 6.546 |
| 20 | chr10: 40657833-40657892 | LOC481318 | 9.395 | 8.074 |
| 21 | chr35: 25780447-25780506 | LOC478739 | 10.051 | 8.782 |
| 22 | chr9: 16688657-16688716 | ENSCAFT00000026424 | 12.434 | 11.181 |
| 23 | chr18: 030484748-030484692 | TC35778 | 10.396 | 9.146 |
| 24 | chr4: 27032249-27032190 | LOC479245 | 11.396 | 10.227 |
| 25 | chr2: 8301693-8301752 | LOC487081 | 8.427 | 7.416 |
| 26 | chr23: 48255077-48255018 | DN877221 | 10.204 | 9.202 |
| 27 | chr5: 34747895-34747836 | ENSCAFT00000025132 | 12.602 | 11.693 |
| 28 | | CO718726 | 8.949 | 9.948 |
| 29 | chr17: 42796352-42796293 | CO683620 | 5.994 | 6.995 |
| 30 | chr23: 11819251-11819307 | LOC485595 | 5.567 | 6.592 |
| 31 | chr28: 38170437-38170496 | LOC477866 | 4.464 | 5.518 |
| 32 | chr20: 6090331-6090272 | LOC484631 | 8.304 | 9.378 |

SUPPL. TABLE 2-continued

SUMMARY:
Mosaic cysts developed from canine MDCK cells were used in microarray experiments to examine the process of cell death and recovery in the epithelial wall. Parts of the cyst were killed and the remainder was allowed to recover. Two populations of cells were examined (G0/G1 and S/G2/M) at 3 different time points (control, 12 and 24 hours after cell wounding).

| | | | | |
|---|---|---|---|---|
| 33 | chr10: 28009942-28009883 | DN270582 | 7.244 | 8.32 |
| 34 | chr13: 4024163-4024222 | LOC481980 | 5.056 | 6.158 |
| 35 | chr6: 9332793-9332852 | CO599122 | 7.086 | 8.203 |
| 36 | | TC45157 | 7.267 | 8.394 |
| 37 | chr35: 27970359-27970300 | TC33171 | 8.008 | 9.21 |
| 38 | chrX: 123180663-123180723 | CO585946 | 7.383 | 8.608 |
| 39 | chr30: 11214095-11214154 | BM538435 | 6.105 | 7.333 |
| 40 | | DN746739 | 8.112 | 9.347 |
| 41 | chr6: 26151795-26150394 | LOC479820 | 5.814 | 7.053 |
| 42 | chr12: 5547078-5547019 | BU746162 | 6.262 | 7.523 |
| 43 | chr10: 59259242-59259301 | LOC481373 | 5.31 | 6.573 |
| 44 | chr5: 18797423-18797364 | CO687246 | 4.973 | 6.263 |
| 45 | chr24: 6287615-6287556 | LOC477136 | 4.96 | 6.255 |
| 46 | | ENSCAFT00000001196 | 6.361 | 7.663 |
| 47 | chr9: 28174571-28174512 | LOC480587 | 6.713 | 8.03 |
| 48 | chr4: 46242856-46242915 | SLIT3 | 7.512 | 8.859 |
| 49 | chr9: 19068479-19068538 | LOC480551 | 9.359 | 10.708 |
| 50 | chr17: 53823173-53823114 | LOC483121 | 7.876 | 9.248 |
| 51 | chr18: 55481178-55481237 | CO590810 | 7.567 | 8.942 |
| 52 | chr25: 51762712-51762653 | DN745414 | 5.174 | 6.554 |
| 53 | chr20: 3117808-3117749 | DN744243 | 9.692 | 11.078 |
| 54 | chr30: 13291922-13291863 | CO591347 | 7.058 | 8.446 |
| 55 | chr20: 42674975-42675034 | TC32323 | 8.91 | 10.304 |
| 56 | chr32: 5953424-5953364 | CO718860 | 4.967 | 6.383 |
| 57 | chr3: 22909627-22909567 | TC45410 | 7.455 | 8.919 |
| 58 | chr18: 26594593-26594534 | BM538045 | 6.691 | 8.162 |

SUPPL. TABLE 2-continued

SUMMARY:
Mosaic cysts developed from canine MDCK cells were used in microarray experiments to examine the process of cell death and recovery in the epithelial wall. Parts of the cyst were killed and the remainder was allowed to recover. Two populations of cells were examined (G0/G1 and S/G2/M) at 3 different time points (control, 12 and 24 hours after cell wounding).

| | | | | |
|---|---|---|---|---|
| 59 | chr18: 25839171-25839230 | LOC475915 | 4.761 | 6.259 |
| 60 | chr28: 15757459-15757518 | MRP2 | 9.003 | 10.502 |
| 61 | chr28: 16678520-16678461 | CO701152 | 7.603 | 9.119 |
| 62 | chr4: 46261653-46261595 | CO719127 | 6.504 | 8.05 |
| 63 | chr34: 6795793-6795734 | LOC478616 | 5.606 | 7.185 |
| 64 | chr13: 6363675-6363616 | DN748424 | 8.442 | 10.028 |
| 65 | chr4: 024919126-024919183 | CO719536 | 10.845 | 12.443 |
| 66 | chr10: 35585025-35583726 | LOC474532 | 4.866 | 6.469 |
| 67 | chr6: 25072093-25072034 | LOC479813 | 5.323 | 6.934 |
| 68 | chr15: 21107956-21107897 | TC39136 | 4.651 | 6.302 |
| 69 | | LOC484069 | 5.507 | 7.165 |
| 70 | chr9: 10810958-10811017 | TC38144 | 7.422 | 9.095 |
| 71 | chr18: 16246118-16241231 | LOC475887 | 8.854 | 10.532 |
| 72 | chr20: 42674280-42674339 | LOC484770 | 7.192 | 8.875 |
| 73 | | CAN2DD | 6.801 | 8.492 |
| 74 | chr15: 17170783-17170724 | LOC475370 | 10.241 | 11.953 |
| 75 | chr7: 21047390-21047331 | LOC480043 | 10.484 | 12.242 |
| 76 | chr6: 34993617-34993558 | DN372532 | 6.369 | 8.146 |
| 77 | chrM: 5798-5857 | TC31728 | 6.99 | 8.782 |
| 78 | chr8: 50575534-50575152 | LOC490784 | 6.451 | 8.251 |
| 79 | chr22: 51481040-51481099 | CF411007 | 7.493 | 9.301 |
| 80 | chr17: 40175227-40175168 | DN445054 | 7.634 | 9.468 |
| 81 | chrX: 123182076-123182017 | LOC492223 | 10.211 | 12.065 |
| 82 | chr20: 42668553-42668686 | ENSCAFT00000018224 | 9.486 | 11.35 |
| 83 | chr38: 4808440-4808381 | DN381350 | 6.012 | 7.92 |
| 84 | chr10: 44084983-44084924 | LOC481328 | 4.873 | 6.783 |

SUPPL. TABLE 2-continued

SUMMARY:
Mosaic cysts developed from canine MDCK cells were used in microarray experiments to examine the process of cell death and recovery in the epithelial wall. Parts of the cyst were killed and the remainder was allowed to recover. Two populations of cells were examined (G0/G1 and S/G2/M) at 3 different time points (control, 12 and 24 hours after cell wounding).

| | | | | |
|---|---|---|---|---|
| 85 | chr27: 39917800-39917741 | LOC486698 | 8.348 | 10.278 |
| 86 | chr4: 42741927-42741986 | LOC489117 | 9.565 | 11.505 |
| 87 | chrX: 32896873-32896814 | RPGR | 5.437 | 7.419 |
| 88 | chr4: 24919372-24919313 | LOC489033 | 10.758 | 12.821 |
| 89 | | LOC484037 | 5.777 | 7.865 |
| 90 | chr22: 51487724-51487662 | CO682886 | 6.934 | 9.046 |
| 91 | chr16: 4927636-4927695 | DN746939 | 8.417 | 10.554 |
| 92 | chr3: 74183674-74183615 | CO695806 | 7.901 | 10.068 |
| 93 | chr12: 22648099-22648269 | CO693697 | 9.386 | 11.622 |
| 94 | | DN746102 | 7.143 | 9.395 |
| 95 | chr4: 17897844-17897785 | LOC479219 | 9.562 | 11.816 |
| 96 | | LOC484300 | 7.802 | 10.083 |
| 97 | chrUn: 19921863-19921922 | VNN1 | 6.612 | 8.903 |
| 98 | chr24: 35699393-35699335 | CO691449 | 8.582 | 10.968 |
| 99 | chr7: 021236162-021236103 | CO692597 | 5.835 | 8.759 |
| 100 | chr5: 24164926-24164985 | TC31721 | 7.692 | 10.998 |

| | GG_24vsGG_C | | | | |
|---|---|---|---|---|---|
| No | M | Fold | AdjP | FDR | B |
| 1 | 2.518 | 5.727 | 9e−05 | 2e−05 | 11.034 |
| 2 | 2.069 | 4.197 | 0.02494 | 0.00038 | 5.897 |
| 3 | 1.887 | 3.699 | 0.03643 | 0.00045 | 5.535 |
| 4 | 1.805 | 3.494 | 0.02933 | 0.00041 | 5.742 |
| 5 | 1.753 | 3.372 | 0.03383 | 0.00042 | 5.606 |
| 6 | 1.744 | 3.35 | 1e−05 | 1e−05 | 12.652 |
| 7 | 1.732 | 3.323 | 0.0319 | 0.00042 | 5.662 |
| 8 | 1.726 | 3.307 | 0.00757 | 0.00021 | 7.027 |
| 9 | 1.693 | 3.234 | 0.01256 | 0.00025 | 6.549 |
| 10 | 1.631 | 3.098 | 0.02176 | 0.00036 | 6.027 |
| 11 | 1.605 | 3.043 | 0.00672 | 0.00021 | 7.139 |
| 12 | 1.603 | 3.037 | 0.00134 | 1e−04 | 8.636 |
| 13 | 1.571 | 2.971 | 0.00922 | 0.00023 | 6.841 |
| 14 | 1.504 | 2.837 | 0.00983 | 0.00024 | 6.781 |
| 15 | 1.482 | 2.793 | 0.04977 | 5e−04 | 5.235 |
| 16 | 1.453 | 2.738 | 0.00639 | 0.00021 | 7.187 |
| 17 | 1.452 | 2.736 | 0.03423 | 0.00042 | 5.595 |
| 18 | 1.383 | 2.608 | 0.0109 | 0.00025 | 6.684 |
| 19 | 1.322 | 2.5 | 0.0032 | 0.00017 | 7.835 |
| 20 | 1.321 | 2.498 | 0.02615 | 0.00038 | 5.852 |
| 21 | 1.269 | 2.41 | 0.01407 | 0.00027 | 6.442 |
| 22 | 1.253 | 2.384 | 0.02549 | 0.00038 | 5.877 |
| 23 | 1.25 | 2.379 | 0.00512 | 2e−04 | 7.395 |
| 24 | 1.169 | 2.248 | 0.02863 | 0.00041 | 5.766 |
| 25 | 1.011 | 2.015 | 0.01872 | 0.00032 | 6.17 |
| 26 | 1.001 | 2.002 | 0.00708 | 0.00021 | 7.091 |
| 27 | 0.909 | 1.878 | 0.04338 | 0.00047 | 5.367 |

SUPPL. TABLE 2-continued

SUMMARY:
Mosaic cysts developed from canine MDCK cells were used in microarray experiments to examine
the process of cell death and recovery in the epithelial wall. Parts of the cyst were
killed and the remainder was allowed to recover. Two populations of cells were examined
(G0/G1 and S/G2/M) at 3 different time points (control, 12 and 24 hours after cell wounding).

| | | | | |
|---|---|---|---|---|
| 28 | −1 | 0.5 | 0.04325 | 0.00047 | 5.37 |
| 29 | −1.001 | 0.5 | 0.04938 | 5e−04 | 5.243 |
| 30 | −1.025 | 0.491 | 0.02917 | 0.00041 | 5.748 |
| 31 | −1.054 | 0.482 | 0.04915 | 5e−04 | 5.247 |
| 32 | −1.074 | 0.475 | 0.04395 | 0.00047 | 5.355 |
| 33 | −1.076 | 0.474 | 0.02967 | 0.00041 | 5.731 |
| 34 | −1.102 | 0.466 | 0.03062 | 0.00041 | 5.701 |
| 35 | −1.117 | 0.461 | 0.01183 | 0.00025 | 6.606 |
| 36 | −1.127 | 0.458 | 0.03379 | 0.00042 | 5.607 |
| 37 | −1.202 | 0.435 | 0.00419 | 0.00019 | 7.583 |
| 38 | −1.224 | 0.428 | 0.02105 | 0.00035 | 6.059 |
| 39 | −1.228 | 0.427 | 0.03165 | 0.00042 | 5.67 |
| 40 | −1.235 | 0.425 | 0.0228 | 0.00037 | 5.983 |
| 41 | −1.239 | 0.424 | 0.01799 | 0.00032 | 6.208 |
| 42 | −1.261 | 0.417 | 0.03887 | 0.00045 | 5.473 |
| 43 | −1.263 | 0.417 | 0.00087 | 7e−05 | 9.031 |
| 44 | −1.29 | 0.409 | 0.00772 | 0.00021 | 7.009 |
| 45 | −1.295 | 0.407 | 0.01268 | 0.00025 | 6.54 |
| 46 | −1.301 | 0.406 | 0.03241 | 0.00042 | 5.647 |
| 47 | −1.317 | 0.401 | 0.01102 | 0.00025 | 6.673 |
| 48 | −1.347 | 0.393 | 0.03769 | 0.00045 | 5.502 |
| 49 | −1.349 | 0.392 | 0.00275 | 0.00015 | 7.975 |
| 50 | −1.371 | 0.387 | 0.03978 | 0.00045 | 5.451 |
| 51 | −1.375 | 0.386 | 0.00145 | 1e−04 | 8.564 |
| 52 | −1.381 | 0.384 | 0.00718 | 0.00021 | 7.078 |
| 53 | −1.386 | 0.383 | 0.02631 | 0.00038 | 5.846 |
| 54 | −1.388 | 0.382 | 0.01699 | 0.00032 | 6.263 |
| 55 | −1.394 | 0.38 | 0.00997 | 0.00024 | 6.768 |
| 56 | −1.415 | 0.375 | 0.04819 | 5e−04 | 5.266 |
| 57 | −1.464 | 0.362 | 0.04045 | 0.00045 | 5.434 |
| 58 | −1.471 | 0.361 | 0.02024 | 0.00034 | 6.096 |
| 59 | −1.498 | 0.354 | 0.00597 | 0.00021 | 7.25 |
| 60 | −1.5 | 0.354 | 0.00723 | 0.00021 | 7.071 |
| 61 | −1.515 | 0.35 | 0.00858 | 0.00022 | 6.91 |
| 62 | −1.547 | 0.342 | 0.01844 | 0.00032 | 6.185 |
| 63 | −1.578 | 0.335 | 5e−05 | 2e−05 | 11.55 |
| 64 | −1.586 | 0.333 | 0.00851 | 0.00022 | 6.918 |
| 65 | −1.598 | 0.33 | 0.01147 | 0.00025 | 6.635 |
| 66 | −1.603 | 0.329 | 2e−05 | 1e−05 | 12.488 |
| 67 | −1.611 | 0.327 | 0.04462 | 0.00047 | 5.34 |
| 68 | −1.651 | 0.319 | 0.0301 | 0.00041 | 5.718 |
| 69 | −1.658 | 0.317 | 0.04663 | 0.00049 | 5.298 |
| 70 | −1.673 | 0.314 | 0.02626 | 0.00038 | 5.848 |
| 71 | −1.678 | 0.312 | 0.00515 | 2e−04 | 7.39 |
| 72 | −1.683 | 0.311 | 0.04074 | 0.00045 | 5.428 |
| 73 | −1.692 | 0.31 | 0.00033 | 5e−05 | 9.913 |
| 74 | −1.712 | 0.305 | 0.00073 | 7e−05 | 9.194 |
| 75 | −1.758 | 0.296 | 0.03869 | 0.00045 | 5.477 |
| 76 | −1.777 | 0.292 | 0.00063 | 6e−05 | 9.336 |
| 77 | −1.792 | 0.289 | 0.00335 | 0.00017 | 7.791 |
| 78 | −1.8 | 0.287 | 0.00803 | 0.00022 | 6.972 |
| 79 | −1.807 | 0.286 | 0.00686 | 0.00021 | 7.121 |
| 80 | −1.834 | 0.281 | 0.00676 | 0.00021 | 7.134 |
| 81 | −1.854 | 0.277 | 0.00024 | 5e−05 | 10.187 |
| 82 | −1.863 | 0.275 | 0.03705 | 0.00045 | 5.519 |
| 83 | −1.908 | 0.266 | 0.01831 | 0.00032 | 6.192 |
| 84 | −1.91 | 0.266 | 0.01578 | 3e−04 | 6.333 |
| 85 | −1.93 | 0.262 | 0.00211 | 0.00013 | 8.221 |
| 86 | −1.94 | 0.261 | 0.00238 | 0.00014 | 8.108 |
| 87 | −1.982 | 0.253 | 0.00042 | 5e−05 | 9.705 |
| 88 | −2.063 | 0.239 | 0.01204 | 0.00025 | 6.59 |
| 89 | −2.088 | 0.235 | 0.03919 | 0.00045 | 5.465 |
| 90 | −2.112 | 0.231 | 0.00035 | 5e−05 | 9.864 |
| 91 | −2.137 | 0.227 | 0.00437 | 0.00019 | 7.544 |
| 92 | −2.167 | 0.223 | 0.02641 | 0.00038 | 5.843 |
| 93 | −2.236 | 0.212 | 0.02304 | 0.00037 | 5.973 |
| 94 | −2.251 | 0.21 | 0.01065 | 0.00025 | 6.706 |
| 95 | −2.254 | 0.21 | 0.00382 | 0.00018 | 7.668 |
| 96 | −2.281 | 0.206 | 0.03796 | 0.00045 | 5.495 |
| 97 | −2.291 | 0.204 | 0.01309 | 0.00026 | 6.51 |
| 98 | −2.386 | 0.191 | 0.00519 | 2e−04 | 7.381 |

SUPPL. TABLE 2-continued

SUMMARY:
Mosaic cysts developed from canine MDCK cells were used in microarray experiments to examine
the process of cell death and recovery in the epithelial wall. Parts of the cyst were
killed and the remainder was allowed to recover. Two populations of cells were examined
(G0/G1 and S/G2/M) at 3 different time points (control, 12 and 24 hours after cell wounding).

| | | | | | |
|---|---|---|---|---|---|
| 99 | −2.924 | 0.132 | 0.00045 | 5e−05 | 9.626 |
| 100 | −3.306 | 0.101 | 0.00112 | 9e−05 | 8.804 |

Group identity is denoted by cell cycle and time point. Codes for each are:
GG: G0/G1 Cells
SGM: S/G2/M Cells
C: control
12: 12 hours post wounding
24: 24 hours post wounding

SUPPLEMENTAL TABLE 3

For real-time PCR,
the following primers were used:

| | |
|---|---|
| WFDC2 | 5'-GCTGGCCTCCTACTAGGGTT-3' |
| | 5'-ACACAGTCCGTAATTGGTTCAAG-3' |
| KIM1 | 5'-GTTAAACCAGAGATTCCCACACG-3' |
| | 5'-TCTCATGGGGACAAAATGTAGTG-3' |
| GAPDH | 5'-AGGTCGGTGTGAACGGATTTG-3' |
| | 5'-TGTAGACCATGTAGTTGAGGTCA-3' |

To prepare the probes for
in situ hybridization, the following
primers were used:

| | |
|---|---|
| Mouse CMF1 | 5'-ATCGGAATTCGACAGTACCAGGACAGCGAC-3' |
| | 5'-ATCGCTCGAGAGAGAGTCACAGCACCTTGC-3' |
| Mouse KIM1 | 5'-ATCGACTAGTAGGCCTCATACTGCTTCTCC-3' |
| | 5'-ATCGCTCGAGATGTTGTCTTCAGCTCGGGA-3' |
| Mouse NAPSA | 5'-ATCGGAATTCACTACGTACCTCCCCTCACC-3' |
| | 5'-ATCGCTCGAGTTTTGAAGAACTGCGCCTGC-3' |
| Mouse SIX2 | 5'-ATCGGGATCCAATGAAAGCGTGCTCAAGGC-3' |
| | 5'-ATCGCTCGAGGAACTGCCTAGCACCGACTT-3' |
| Mouse SOX9 | 5'-ATCGGGATCCCCAGCAAGAACAAGCCACAC-3' |
| | 5'-ATCGCTCGAGGGCTCAGTTCACCGATGTCCA-3' |
| Mouse TCFAP2B | 5'-ATCGGAATTCGTGACATCGAGAGACGCGAT-3' |
| | 5'-ATCGCTCGAGTGGCTAAGGAAAGCATGGGG-3' |
| Mouse UMOD | 5'-ATCGGAATTCAGATCCAGGTGAAGGCTTGC-3' |
| | 5'-ATCGCTCGAGTCCCACCCAAGCTGATGTTC-3' |
| Mouse WFDC2 | 5'-ATCGACTAGTATTACGGACTGTGTGTTGGA-3' |
| | 5'-ATCGCTCGAGCTTCGTGGAGACTTGACCTC-3' |
| Human KIM1 | 5'-ATCGGGATCCCCACGTCACCTATCGGAAGG-3' |
| | 5'-ATCGCTCGAGTGCTGGCTGAGGTGAAGATG-3' |
| Human WFDC2 | 5'-ATCGGGATCCATAGCACCATGCCTGCTTGT-3' |
| | 5'-ATCGCTCGAGTGGTTGGGAAAGGGAGAAGC-3' |

Additional Information and Data

The wild-type protein sequence of human WFDC2 is provided below:

(SEQ ID NO: 1)
MPACRLGPLAAALLLSLLLFGFTLVSGTGAEKTGVCPELQADQNCTQ

ECVSDSECADNLKCCSAGCATFCSLPNDKEGSCPQVNINFPQLGLCR

DQCQVDSQCPGQMKCCRNGCGKVSCVTPNF

Only one N-linked glycosylation site was predicted in human WFDC2. We made the N44D mutation and its sequence is as follows (SEQ ID NO: 8)
MPACRLGPLAAALLLSLLLFGFTLVSGTGAEKTGVCPELQADQDCTQ

ECVSDSECADNLKCCSAGCATFCSLPNDKEGSCPQVNINFPQLGLCR

DQCQVDSQCPGQMKCCRNGCGKVSCVTPNF

This mutant protein, when C terminal fused with GFP protein, is secreted normally, but failed to rescue the WFDC2 knockout phenotypes observed in our 3D cell culture model.

Currently, WFDC2 1-30 amino acid is predicted to be the signal peptide region, but previously 1-21 was (shown below). We C terminal fused the following sequence with GFP, and the fusion protein was secreted, suggesting it is sufficient for the extracellular targeting. However, this fusion protein failed to rescue, suggesting it is not required for the therapeutic related activities.

(SEQ ID NO: 9)
MPACR LGPLA AALLL SLLLF G

It is understood that the examples and embodiments described herein are for illustrative purposes only and that various modifications or changes in light thereof will be suggested to persons skilled in the art and are to be included within the spirit and purview of this application and scope of the appended claims. All publications, sequence accession numbers, patents, and patent applications cited herein are hereby incorporated by reference in their entirety for all purposes.

What is claimed is:

1. A method of treating acute kidney injury in a human, the method comprising administering to the human a sufficient amount of a polypeptide comprising an amino acid sequence at least 95% identical to SEQ ID NO:1, to reduce at least one symptom of the acute kidney injury.

2. The method of claim 1, wherein the polypeptide comprises SEQ ID NO:1.

3. The method of claim 1, wherein the amino acid sequence is linked to a protein sequence that extends the circulating half-life in the blood of the polypeptide.

4. The method of claim 1, wherein the amino acid sequence is linked to an antibody Fc domain or human serum albumin.

5. The method of claim 4, wherein the amino acid sequence is linked to an antibody Fc domain that has been mutated to prolong the circulating half-life of polypeptide.

6. The method of claim 1, wherein the polypeptide is PEGylated.

7. The method of claim 1, wherein the polypeptide comprises at least one non-naturally-encoded amino acid.

8. The method of claim 1, wherein the polypeptide is administered intravenously, orally, inhalationally, nasally, rectally, intraperitoneally, parenterally, intramuscularly, subcutaneously, or transdermally.

* * * * *

SEQUENCE LISTING

<160> NUMBER OF SEQ ID NOS: 39

<210> SEQ ID NO 1
<211> LENGTH: 124
<212> TYPE: PRT

<213> ORGANISM: Homo sapiens

<400> SEQUENCE: 1

Met Pro Ala Cys Arg Leu Gly Pro Leu Ala Ala Leu Leu Leu Ser
1               5                   10                  15

Leu Leu Leu Phe Gly Phe Thr Leu Val Ser Gly Thr Gly Ala Glu Lys
                20                  25                  30

Thr Gly Val Cys Pro Glu Leu Gln Ala Asp Gln Asn Cys Thr Gln Glu
            35                  40                  45

Cys Val Ser Asp Ser Glu Cys Ala Asp Asn Leu Lys Cys Cys Ser Ala
        50                  55                  60

Gly Cys Ala Thr Phe Cys Ser Leu Pro Asn Asp Lys Glu Gly Ser Cys
65                  70                  75                  80

Pro Gln Val Asn Ile Asn Phe Pro Gln Leu Gly Leu Cys Arg Asp Gln
                85                  90                  95

Cys Gln Val Asp Ser Gln Cys Pro Gly Gln Met Lys Cys Cys Arg Asn
            100                 105                 110

Gly Cys Gly Lys Val Ser Cys Val Thr Pro Asn Phe
            115                 120

<210> SEQ ID NO 2
<211> LENGTH: 124
<212> TYPE: PRT
<213> ORGANISM: Canis lupus familiaris

<400> SEQUENCE: 2

Met Pro Ala Cys Arg Pro Gly Pro Leu Ala Gly Ala Leu Leu Leu Gly
1               5                   10                  15

Leu Leu Leu Leu Gly Leu Pro Arg Val Pro Gly Gly Glu Val Glu Lys
                20                  25                  30

Thr Gly Val Cys Pro Gln Leu Gln Ala Asp Leu Asn Cys Thr Gln Glu
            35                  40                  45

Cys Val Ser Asp Ala Gln Cys Ala Asp Asn Leu Lys Cys Cys Gln Ala
        50                  55                  60

Gly Cys Ala Thr Ile Cys His Leu Pro Asn Glu Lys Glu Gly Ser Cys
65                  70                  75                  80

Pro Gln Val Asn Thr Asp Phe Pro Gln Leu Gly Leu Cys Gln Asp Gln
                85                  90                  95

Cys Gln Val Asp Ser His Cys Pro Gly Leu Leu Lys Cys Cys Tyr Asn
            100                 105                 110

Gly Cys Gly Lys Val Ser Cys Val Thr Pro Ile Phe
            115                 120

<210> SEQ ID NO 3
<211> LENGTH: 123
<212> TYPE: PRT
<213> ORGANISM: Oryctolagus cuniculus

<400> SEQUENCE: 3

Met Pro Ala Ser Arg Leu Val Pro Leu Gly Ala Val Leu Leu Leu Gly
1               5                   10                  15

Leu Leu Leu Leu Leu Glu Leu Pro Val Thr Gly Thr Gly Ala Asp
                20                  25                  30

Lys Pro Gly Val Cys Pro Gln Leu Ser Ala Asp Leu Asn Cys Thr Gln
            35                  40                  45

Asp Cys Arg Ala Asp Gln Asp Cys Ala Glu Asn Leu Lys Cys Cys Arg
        50                  55                  60

```
Ala Gly Cys Ser Ala Ile Cys Ser Ile Pro Asn Glu Lys Glu Gly Ser
 65                  70                  75                  80

Cys Pro Ser Ile Asp Phe Pro Gln Leu Gly Ile Cys Gln Asp Leu Cys
                 85                  90                  95

Gln Val Asp Ser Gln Cys Pro Gly Lys Met Lys Cys Cys Leu Asn Gly
            100                 105                 110

Cys Gly Lys Val Ser Cys Val Thr Pro Asn Phe
        115                 120
```

```
<210> SEQ ID NO 4
<211> LENGTH: 168
<212> TYPE: PRT
<213> ORGANISM: Rattus norvegicus

<400> SEQUENCE: 4

Met Pro Ala Cys Arg Leu Cys Leu Leu Ala Thr Gly Leu Leu Leu Gly
  1               5                  10                  15

Leu Leu Leu Phe Thr Pro Leu Ser Ala Thr Gly Thr Arg Ala Glu Lys
                 20                  25                  30

Pro Gly Val Cys Pro Gln Leu Glu Pro Ile Thr Asp Cys Val Lys Ala
             35                  40                  45

Cys Ile Leu Asp Asn Asp Cys Gln Asp Asn Tyr Lys Cys Cys Gln Ala
 50                  55                  60

Gly Cys Gly Ser Val Cys Ser Lys Pro Asn Gly Leu Ser Glu Gly Lys
 65                  70                  75                  80

Leu Ser Arg Thr Ala Thr Gly Thr Thr Thr Leu Ser Ala Gly Leu Ala
                 85                  90                  95

Arg Thr Ser Pro Leu Ser Arg Gly Gln Val Ser Thr Lys Pro Pro Val
            100                 105                 110

Val Thr Lys Glu Gly Gly Asn Gly Glu Lys Gln Gly Thr Cys Pro Ser
        115                 120                 125

Val Asp Phe Pro Lys Leu Gly Leu Cys Glu Asp Gln Cys Gln Met Asp
130                 135                 140

Ser Gln Cys Ser Gly Asn Met Lys Cys Cys Arg Asn Gly Cys Gly Lys
145                 150                 155                 160

Met Gly Cys Thr Thr Pro Lys Phe
                165
```

```
<210> SEQ ID NO 5
<211> LENGTH: 174
<212> TYPE: PRT
<213> ORGANISM: Mus musculus

<400> SEQUENCE: 5

Met Pro Ala Cys Arg Leu Cys Leu Leu Ala Ala Gly Leu Leu Leu Gly
  1               5                  10                  15

Leu Leu Leu Phe Thr Pro Ile Ser Ala Thr Gly Thr Asp Ala Glu Lys
                 20                  25                  30

Pro Gly Glu Cys Pro Gln Leu Glu Pro Ile Thr Asp Cys Val Leu Glu
             35                  40                  45

Cys Thr Leu Asp Lys Asp Cys Ala Asp Asn Arg Lys Cys Cys Gln Ala
 50                  55                  60

Gly Cys Ser Ser Val Cys Ser Lys Pro Asn Gly Pro Ser Glu Gly Glu
 65                  70                  75                  80

Leu Ser Gly Thr Asp Thr Lys Leu Ser Glu Thr Gly Thr Thr Thr Gln
                 85                  90                  95
```

Ser Ala Gly Leu Asp His Thr Thr Lys Pro Pro Gly Gly Gln Val Ser
            100                 105                 110

Thr Lys Pro Pro Ala Val Thr Arg Glu Gly Leu Gly Val Arg Glu Lys
        115                 120                 125

Gln Gly Thr Cys Pro Ser Val Asp Ile Pro Lys Leu Gly Leu Cys Glu
    130                 135                 140

Asp Gln Cys Gln Val Asp Ser Gln Cys Ser Gly Asn Met Lys Cys Cys
145                 150                 155                 160

Arg Asn Gly Cys Gly Lys Met Ala Cys Thr Thr Pro Lys Phe
                165                 170

<210> SEQ ID NO 6
<211> LENGTH: 123
<212> TYPE: PRT
<213> ORGANISM: Sus scrofa

<400> SEQUENCE: 6

Met Pro Ala Cys Arg Leu Gly Leu Leu Val Ala Ser Leu Leu Leu Gly
1               5                   10                  15

Leu Leu Leu Gly Leu Pro Pro Val Thr Gly Thr Gly Ala Glu Lys Ser
            20                  25                  30

Gly Val Cys Pro Ala Val Glu Val Asp Met Asn Cys Thr Gln Glu Cys
        35                  40                  45

Leu Ser Asp Ala Asp Cys Ala Asp Asn Leu Lys Cys Cys Lys Ala Gly
    50                  55                  60

Cys Val Thr Ile Cys Gln Met Pro Asn Glu Lys Glu Gly Ser Cys Pro
65                  70                  75                  80

Gln Val Asp Ile Ala Phe Pro Gln Leu Gly Leu Cys Leu Asp Gln Cys
                85                  90                  95

Gln Val Asp Ser Gln Cys Pro Gly Gln Leu Lys Cys Cys Arg Asn Gly
            100                 105                 110

Cys Gly Lys Val Ser Cys Val Thr Pro Val Phe
        115                 120

<210> SEQ ID NO 7
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 7

His His His His His His
1               5

<210> SEQ ID NO 8
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Met Pro Ala Cys Arg Leu Gly Pro Leu Ala Ala Ala Leu Leu Leu Ser
1               5                   10                  15

Leu Leu Leu Phe Gly Phe Thr Leu Val Ser Gly Thr Gly Ala Glu Lys
            20                  25                  30

Thr Gly Val Cys Pro Glu Leu Gln Ala Asp Gln Asp Cys Thr Gln Glu
            35                  40                  45

Cys Val Ser Asp Ser Glu Cys Ala Asp Asn Leu Lys Cys Cys Ser Ala
 50                  55                  60

Gly Cys Ala Thr Phe Cys Ser Leu Pro Asn Asp Lys Glu Gly Ser Cys
 65                  70                  75                  80

Pro Gln Val Asn Ile Asn Phe Pro Gln Leu Gly Leu Cys Arg Asp Gln
                85                  90                  95

Cys Gln Val Asp Ser Gln Cys Pro Gly Gln Met Lys Cys Cys Arg Asn
            100                 105                 110

Gly Cys Gly Lys Val Ser Cys Val Thr Pro Asn Phe
            115                 120

<210> SEQ ID NO 9
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Met Pro Ala Cys Arg Leu Gly Pro Leu Ala Ala Ala Leu Leu Leu Ser
 1               5                  10                  15

Leu Leu Leu Phe Gly
            20

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
gctggcctcc tactagggtt                                               20

<210> SEQ ID NO 11
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
acacagtccg taattggttc aag                                           23

<210> SEQ ID NO 12
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
gttaaaccag agattcccac acg                                           23

<210> SEQ ID NO 13
<211> LENGTH: 23
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 13
tctcatgggg acaaaatgta gtg                                            23

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
aggtcggtgt gaacggattt g                                              21

<210> SEQ ID NO 15
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
tgtagaccat gtagttgagg tca                                            23

<210> SEQ ID NO 16
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
atcggaattc gacagtacca ggacagcgac                                     30

<210> SEQ ID NO 17
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
atcgctcgag agagagtcac agcaccttgc                                     30

<210> SEQ ID NO 18
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
atcgactagt aggcctcata ctgcttctcc                                     30

<210> SEQ ID NO 19
<211> LENGTH: 30
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 19
atcgctcgag atgttgtctt cagctcggga                                          30

<210> SEQ ID NO 20
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
atcggaattc actacgtacc tcccctcacc                                          30

<210> SEQ ID NO 21
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
atcgctcgag ttttgaagaa ctgcgcctgc                                          30

<210> SEQ ID NO 22
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
atcgggatcc aatgaaagcg tgctcaaggc                                          30

<210> SEQ ID NO 23
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
atcgctcgag gaactgccta gcaccgactt                                          30

<210> SEQ ID NO 24
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
atcgggatcc ccagcaagaa caagccacac                                          30

<210> SEQ ID NO 25
<211> LENGTH: 30
<212> TYPE: DNA
<213> ORGANISM: Artificial Sequence
<220> FEATURE:
<223> OTHER INFORMATION: Description of Artificial Sequence: Synthetic
``` primer

<400> SEQUENCE: 25
atcgctcgag gctcagttca ccgatgtcca                                30

<210> SEQ ID NO 26
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
atcggaattc gtgacatcga gagacgcgat                                30

<210> SEQ ID NO 27
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
atcgctcgag tggctaagga aagcatgggg                                30

<210> SEQ ID NO 28
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
atcggaattc agatccaggt gaaggcttgc                                30

<210> SEQ ID NO 29
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
atcgctcgag tcccacccaa gctgatgttc                                30

<210> SEQ ID NO 30
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
atcgactagt attacggact gtgtgttgga                                30

<210> SEQ ID NO 31
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 31
atcgctcgag cttcgtggag acttgacctc                                    30

<210> SEQ ID NO 32
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
atcgggatcc ccacgtcacc tatcggaagg                                    30

<210> SEQ ID NO 33
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
atcgctcgag tgctggctga ggtgaagatg                                    30

<210> SEQ ID NO 34
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
atcgggatcc atagcaccat gcctgcttgt                                    30

<210> SEQ ID NO 35
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
atcgctcgag tggttgggaa agggagaagc                                    30

<210> SEQ ID NO 36
<211> LENGTH: 16
<212> TYPE: PRT
<213> ORGANISM: Canis lupus familiaris
<220> FEATURE:
<221> NAME/KEY: MOD_RES
<222> LOCATION: (1)..(2)
<223> OTHER INFORMATION: Carbamidomethyl Cys
<220> FEATURE:
<221> NAME/KEY: MOD_RES
<222> LOCATION: (6)..(6)
<223> OTHER INFORMATION: Carbamidomethyl Cys
<220> FEATURE:
<221> NAME/KEY: MOD_RES
<222> LOCATION: (10)..(10)
<223> OTHER INFORMATION: Carbamidomethyl Cys

<400> SEQUENCE: 36

Cys Cys Gln Ala Gly Cys Ala Thr Ile Cys His Leu Pro Asn Glu Lys
1               5                   10                  15
```

```
<210> SEQ ID NO 37
<211> LENGTH: 32
<212> TYPE: PRT
<213> ORGANISM: Canis lupus familiaris
<220> FEATURE:
<221> NAME/KEY: MOD_RES
<222> LOCATION: (4)..(4)
<223> OTHER INFORMATION: Carbamidomethyl Cys
<220> FEATURE:
<221> NAME/KEY: MOD_RES
<222> LOCATION: (17)..(17)
<223> OTHER INFORMATION: Carbamidomethyl Cys
<220> FEATURE:
<221> NAME/KEY: MOD_RES
<222> LOCATION: (21)..(21)
<223> OTHER INFORMATION: Carbamidomethyl Cys
<220> FEATURE:
<221> NAME/KEY: MOD_RES
<222> LOCATION: (27)..(27)
<223> OTHER INFORMATION: Carbamidomethyl Cys

<400> SEQUENCE: 37

Gln Gly Ser Cys Pro Gln Val Asn Thr Asp Phe Pro Gln Leu Gly Leu
1               5                   10                  15

Cys Gln Asp Gln Cys Gln Val Asp Ser His Cys Pro Gly Leu Leu Lys
            20                  25                  30

<210> SEQ ID NO 38
<211> LENGTH: 34
<212> TYPE: DNA
<213> ORGANISM: Canis lupus familiaris

<400> SEQUENCE: 38
cgtgtgcccc cagctacagg cggacctgaa ctgt                              34

<210> SEQ ID NO 39
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
cgtgtgcccc caacctgaac tgt                                          23
```